(12) United States Patent
Xia et al.

(10) Patent No.: US 10,130,566 B2
(45) Date of Patent: Nov. 20, 2018

(54) HOLLOW CALCIUM PHOSPHATE PARTICLES

(71) Applicant: PSILOX AB, Göteborg (SE)

(72) Inventors: Wei Xia, Uppsala (SE); Håkan Engqvist, Östhammar (SE)

(73) Assignee: PSILOX AB, Göteborg (SE)

( * ) Notice: Subject to any disclaimer, the term of this patent is extended or adjusted under 35 U.S.C. 154(b) by 97 days.

(21) Appl. No.: 14/778,825

(22) PCT Filed: Mar. 24, 2014

(86) PCT No.: PCT/SE2014/050352
§ 371 (c)(1),
(2) Date: Sep. 21, 2015

(87) PCT Pub. No.: WO2014/148997
PCT Pub. Date: Sep. 25, 2014

(65) Prior Publication Data
US 2016/0051453 A1 Feb. 25, 2016

(30) Foreign Application Priority Data

Mar. 22, 2013 (SE) ...................................... 1350371
Jul. 4, 2013 (SE) ...................................... 1350838
Oct. 1, 2013 (SE) ...................................... 1351150
Feb. 12, 2014 (SE) ...................................... 1450158

(51) Int. Cl.
| | | |
|---|---|---|
| A61K 8/02 | (2006.01) | |
| A61Q 11/00 | (2006.01) | |
| A61K 8/24 | (2006.01) | |
| A61L 27/12 | (2006.01) | |
| A61L 27/56 | (2006.01) | |
| A61K 6/00 | (2006.01) | |
| A61K 8/42 | (2006.01) | |
| A61K 8/20 | (2006.01) | |
| B01J 13/02 | (2006.01) | |

(52) U.S. Cl.
CPC .......... *A61K 8/0279* (2013.01); *A61K 6/0008* (2013.01); *A61K 6/0085* (2013.01); *A61K 8/20* (2013.01); *A61K 8/24* (2013.01); *A61K 8/42* (2013.01); *A61L 27/12* (2013.01); *A61L 27/56* (2013.01); *A61Q 11/00* (2013.01); *B01J 13/02* (2013.01); *A61K 2800/413* (2013.01); *A61L 2400/12* (2013.01)

(58) Field of Classification Search
None
See application file for complete search history.

(56) References Cited

U.S. PATENT DOCUMENTS 9,205,035 B2 * 12/2015 Engqvist ................ A61K 6/033
2012/0134919 A1 5/2012 Engqvist et al.

FOREIGN PATENT DOCUMENTS

| CN | 101428779 A | 5/2009 |
|---|---|---|
| WO | 2007/067561 A2 | 6/2007 |
| WO | WO-2011016772 A1 | 2/2011 |

OTHER PUBLICATIONS

Blumenthal et al. "Stabilization of Amorphous Calcium Phosphate by Mg and ATP" 1977.*
Qi et al. "Highly Stable Amorphous Calcim Phosphate Porous Nanospheres Microwave-Assisted Rapid Synthesis Using ATP as Phosphorous source and Stabilizer, and Their Application in Anticancer Drug Delivery". Nov. 2012.*
Preparation and property of magnesium-substituted hydroxyapatite, Li Zhi-hong et al., Functional Material, vol. 41 No. 4, pp. 700-703 and 708, published on Apr. 20, 2010.
Zhang, et al., "Evolution of the Magnesium incorporated Amorphous Calcium Phosphate to Nano-crystallized Hydroxyapatite in Alkaline Solution", Journal of Crystal Growth 336 (2011) 60-66.
Wang, et al., "Microwave-assisted Synthesis of Hydroxyapatite Hollow Microspheres in Aqueous Solution", Materials Letter 65 (2011) 2361-2363.
Wang, et al., "Preparation of Hollow Hydroxyapatite Microspheres", J. Mater Sci: Mater Med (200) 17:641-646.
Xiaojing Zhang et al: Nanostructured hollow spheres of hydroxyapatite: preparation and potential application in drug delivery, In: Front. Chem. Sci. Eng. 2012, 6(3);246-252.
Kaili Lin et al: Facile synthesis of hydroxyapatite nanoparticles, nanowires and hollow nano-structured microspheres using similar structured hard-precursors, In: Nanoscale, 2011, 3:3052-5.
Ruixue Sun et al: Preparation and characterization of hollow hydroxyapatite microspheres by spray drying method, In: Materials Science and Engineering C 29 (2009) 1088-1092.
International Search Report for PCT/SE2014/050352, ISA/SE, Stockholm, dated Jun. 17, 2014.

* cited by examiner

*Primary Examiner* — Robert A Wax
*Assistant Examiner* — Danah Al-Awadi
(74) *Attorney, Agent, or Firm* — Harness, Dickey & Pierce, P.L.C.

(57) ABSTRACT

The object is the invention is to provide hollow, and preferably porous, spherical CaP particles preferably without the use of strontium ions. This is achieved by a method comprising the steps: a) Providing an aqueous buffer solution of purified water having a pH of 6-10 comprising 20-200 mM sodium ions, 0.1-10 mM potassium ions and 1-10 mM phosphate ions, and wherein the buffer solution is essentially free from strontium; b) adding calcium ions in the range of from 0.1 to less than 2 mM, and magnesium ions in the range of 0.01-5 mM to the buffer solution and forming a mixture; c) heating the mixture of step b) at 60-200° C. for at least 5 minutes d) isolating the formed particles; and e) optionally washing the isolated particles using a suitable solvent. The particles comprise 40-70 weight % of calcium, 20-40 weight % of phosphate and 1-25 weight % magnesium. The Ca/P weight ratio is in the range of 1.10 to 1.90 and more than 80 % of the particles have a particle size between 200 to 1500 nm. The particles are essentially free from strontium. A composition comprising the particles may be used for remineralization of teeth or as bone void filling material.

16 Claims, 21 Drawing Sheets
(8 of 21 Drawing Sheet(s) Filed in Color)

HOLLOW CALCIUM PHOSPHATE PARTICLES

CROSS-REFERENCE TO RELATED APPLICATIONS

This application is a 371 U.S. National Stage of International Application No. PCT/SE2012/050352, filed Mar. 24, 2014, which claims the benefit of and priority to Swedish Patent Applications Nos. 1350371-9, filed Mar. 22, 2013; 1350838-7, filed Jul. 4, 2013; 1351150-6, filed Oct. 1, 2013; and 1450158-9, filed Feb. 12, 2014. The entire disclosures of all of the above applications are incorporated herein by reference.

TECHNICAL FIELD OF THE INVENTION

The present invention relates to a method of producing hollow calcium phosphate particles. The invention further relates to a composition comprising said particles and its use in dental and medical applications.

BACKGROUND OF THE INVENTION

Calcium phosphates (CaP) and in particular hydroxyapatite ($Ca_{10}(PO_4)_6(OH)_2$, HA), is a mineral that is widely used in medical applications due to its similarity to the mineral components of bone and teeth and its biocompatibility. Furthermore hydroxyapatite is non-toxic, biocompatible and bioactive. This means that hydroxyapatite is not harmful and not recognized as a foreign body and on the other hand that it may have positive effects on remodelling of bone. Hence hydroxyapatite has been widely used in bone repair and as drug/gene delivery vehicle, catalyst, ion adsorption/exchange agent, photoelectric regent, etc. Resorbable nanoparticles (i.e. particles that can be dissolved in vivo) are of special interest for a number of applications, e.g. bone void fillers, drug delivery vehicle, desensitization of dentin tubuli, etc.

Calcium phosphates, such as hydroxyapatite and tricalcium phosphate, are widely used in biomedical applications because of their good biocompatibility, bioactivity, and similarity to bone minerals. The morphology, structure, and size of calcium phosphate particles can influence the properties in their applications in hard tissue repair and regeneration, drug/gene delivery, protein adsorption, catalysis, and ion adsorption/exchange etc. Particles with spherical shape and large pore volume are good candidates for drug delivery, protein and ion adsorption, and bone and teeth fillers. So they have attracted more and more attentions recently.

Calcium phosphates, such as hydroxyapatite, spontaneously grow like flakes, fibers or rods by wet chemical methods. Spherical calcium phosphates have only been prepared using structure directing agents, such as ion substituents, surfactants and biomolecules. The present inventors showed in WO2011/016772 that strontium ions affected the morphology of calcium phosphates to form hollow spheres.

Not all morphologies are convenient to serve as delivery particles, catalyst support, ion adsorption/exchange agent, etc., until now when for example rod, tubular, sheet or spherical shaped nanoparticles have been investigated. By way of example, to make a drug delivery process efficient, high surface areas and porous structures are advantageous to adsorb as much active substance as possible and, of course, there is as well the requirement of biocompatibility and an interaction between carrier and substance.

One problem for the preparation of CaP particles is to control size distribution and shape of the particles. Often the size distribution is wide and caused by the hexagonal symmetry and the lattice parameters of CaP. Most likely an orientation along the c-axis and therewith a pin-like shape occurs.

Furthermore hollow particles that are not formed by using tedious techniques or through the use of additives or substitution ions that might jeopardize authorial approval is also wanted.

SUMMARY OF THE INVENTION

The object of the present invention is to provide, hollow and preferably porous, spherical CaP particles preferably without the use of strontium ions and a method of preparing these particles. The method of the present invention is much simpler, cheaper and faster than methods disclosed by prior art.

In a first aspect the present invention relates to a spherical particle having a hollow core and a shell wherein the particle comprises 40-70 weight % of calcium, 20-40 weight % of phosphate and 1-25 weight % magnesium, and wherein the Ca/P molar ratio is in the range of 1.10 to 1.90, and wherein the particle size is 3 µm or less, preferably less than 1 µm.

In a second aspect the present invention relates to a method of preparing the particles according to the present invention wherein the method comprises:
  a) providing an aqueous buffer solution of purified water having a pH of 2 to 10 comprising sodium, potassium and phosphate ions, wherein the concentration of said ions are 20 to 200 mM for sodium, 0.1-10 mM for potassium and 1-10 mM for phosphate;
  b) adding calcium ions in the range of 0.1-5 mM, and magnesium ions in the range of 0.01-5 mM to the buffer solution and forming a mixture;
  c) heating the mixture of step b) at 60 to 200° C. for at least 2 minutes;
  d) isolating the formed particles; and
  e) optionally washing the isolated particles using a suitable solvent.

In a third aspect the present invention relates to a bleaching paste comprising particles according to the present invention and a paste forming compound, and wherein the particles further comprises a bleaching agent such as a peroxide.

In a fourth aspect the present invention relates to a toothpaste comprising particles according to the present invention.

In a fifth aspect the present invention relates to an implant material comprising the particles of the present invention.

In a sixth aspect the present invention relates to particles obtained from the method of the present invention.

In a seventh aspect the present invention relates to a bone void filling material comprising the particles or the composition according to the present invention.

In an eighth aspect the present invention relates to a dental filling material comprising the particles or the composition according to the present invention.

In a ninth aspect the present invention relates to the use of the particles or the composition for treating exposed dental tubuli and/or for remineralization of teeth.

In a tenth aspect the present invention relates to a composition comprising spherical particles and, a paste forming compound; wherein the particles have a hollow core and a shell wherein the particle comprises 40-70 weight % of calcium, 20-40 weight % of phosphate and 1-25 weight % magnesium, and wherein the Ca/P weight ratio is in the range of 1.10 to 1.90, and wherein the mean particle size is 1 μm or less and wherein the particles are essentially free from strontium.

BRIEF DESCRIPTION OF FIGURES

The patent or application file contains at least one drawing executed in color. Copies of this patent with color drawings will be provided by the Patent and Trademark Office upon request and payment of necessary fee.

DETAILED DESCRIPTION OF INNOVATION

In the present invention the term "paste forming compound" relates to compounds that may be mixed with the particles of the present invention to make a paste. The paste forming compound increases the viscosity of the mixture when added to the particles. Non-limiting examples of paste forming compounds are glycerol, polyethylene glycol, polyvinyl alcohol and polysaccharides such as cellulose, hyaluronan and chitosan.

The chemical formula for stoichiometric hydroxyapatite (HA) is $Ca_{10}(PO_4)_6(OH)_2$, but for the purpose of this application many variations can be used. The present invention is mainly described in terms calcium phosphates (CaP) which includes but is not limited to dicalcium phosphate dihydrate (DCPD), octacalcium phosphate (OCP), tricalcium phosphate (TCP), and amorphous calcium phosphate (ACP) or any derivative thereof. Diverse ions can be incorporated in the three sub-lattices (calcium, phosphate and hydroxide lattice) and therewith the properties of the material, as for example solubility, crystal structure, degree of crystallinity, crystal size or porosity, may be changed. Potentially, cationic substitution ions are $Si^{4+}$, $Zn^{2+}$, $Ba^{2+}$, $Fe^{3+}$ or $Ti^{4+}$ and anionic substitution ions are $Cl^-$, $F^-$, $HCO_3^-$ or $CO_3^{2-}$. The source for the ion substitutions can be soluble salts and slightly-soluble salts containing the ions to be substituted, such as but not limited to $Na_2SiO_3$, calcium silicates such as ($CaOSiO_2$, $CaO(SiO_2)_2$, $CaO(SiO_2)_3$); $ZnCl_2$, $ZnSO_4$, $BaCl_2$, $FeCl_3$, $Fe(NO_3)_3$, $Na_2CO_3$, $NaF$, $Na_2FPO_4NaHCO_3$ or $NaTiO_3$ or suitable magnesium source.

Figure 1:
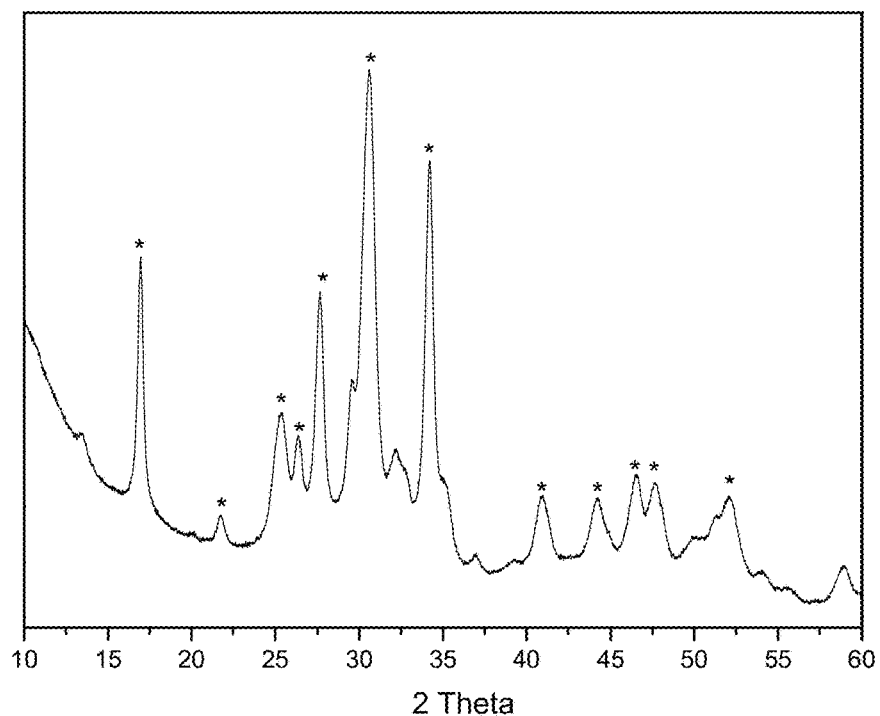
FIG. 1. XRD pattern of calcium phosphate hollow spheres (*: calcium phosphate (045-0136)): The main crystalline phase is the calcium phosphate, but it also contains amorphous phase. The broad peak means that the sample contains nanocrystals.
Figure 2:
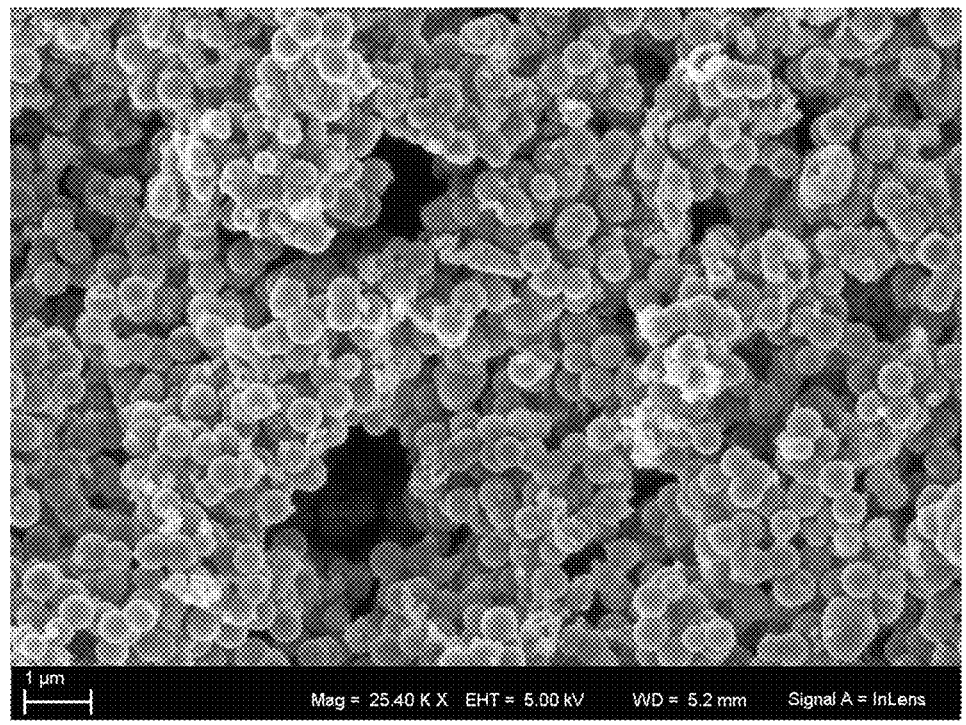
FIG. 2. SEM image of calcium phosphate hollow spheres.
Figure 3:
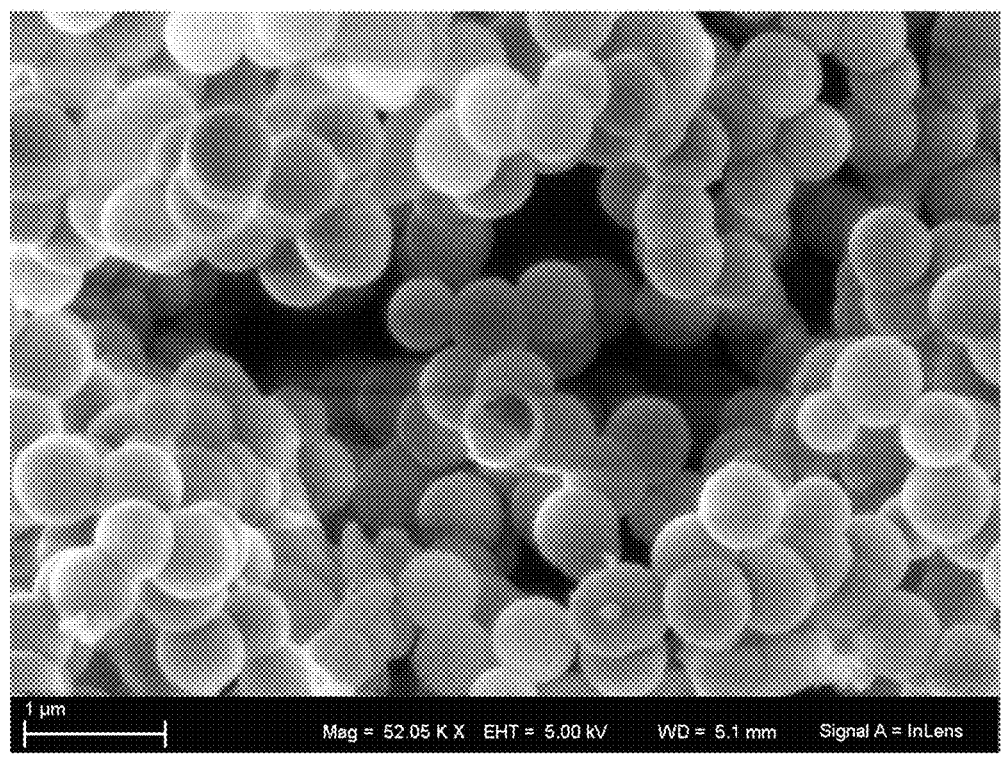
FIG. 3. SEM image of calcium phosphate hollow spheres.

The present application discloses a method of preparing hollow spherical particles of calcium phosphate without the use of templates or sintering steps, instead the present invention is a method that is temperature driven, see FIG. 1-3.

Compared to previous ion doped calcium phosphate spheres, the present invention is a temperature driven process and in comparison with prior art that needs to add strontium to obtain a hollow morphology the method presented herein is not dependent on strontium. By developing a method that is not dependent on the use of strontium, the present inventors facilitates a production method of hollow calcium phosphates that is much cheaper and from a regulatory point of view much easier to get approved.

The Particles

The particles of the present invention comprise 40-70 weight % of calcium (Ca), 20-40 weight % of phosphate ($PO_4$) and 1-25 weight % magnesium (Mg). The particles may contain other ions as well. In one embodiment the concentration of magnesium is 3-15 weight %. In another embodiment the concentration of magnesium is 1-10 weight %. In one embodiment the particles comprise 55-65 weight % of calcium, 25-35 weight % of phosphate and 3-15 weight % of magnesium. The Ca/P molar ratio may be between 1.10 and 1.90, for example 1.10 and 1.70. In one embodiment the ratio is 1.30 to 1.70. In one embodiment the ratio is 1.40 to 1.50. The particles may contain some trace amounts of potassium and/or sodium since they are used in the buffer solution as counter ions. However, these counter ions have not been detected when the particles have been analysed with EDS.

The particles of the present invention may comprise other ions, so called substitution ions. A non-limiting list of cationic ions are $Si^{4+}$, $Zn^{2+}$, $Ba^{2+}$, $Fe^{3+}$ or $Ti^{4+}$ and a non-limiting list of anionic substitution ions are $Cl^-$, $F^-$, $HCO_3$ or $CO_3^2$. In one embodiment the particles are essentially free from strontium, for example less than 1 weight %, or less than 0.5 weight %, or less than 0.1 weight %, or less than 0.01 weight %. In one embodiment the particles of the present invention does not contain strontium. In one embodiment the particles further comprise at least one of the ions selected from silicon, zinc and fluoride.

The mean particle size, the diameter, should be small, preferably not more than 3 μm. This to getter a higher surface area per mass but also in order to easier fill voids, to facilitate the particles to enter and fill dental tubuli. The size should not be too small since it makes it harder to make a paste suitable as a tooth paste or as a bleaching paste. Without being bound by theory, the size is also believed to influence the particles ability to stick to the teeth. In one embodiment the particles are 2 μm or less, or 1 μm or less, or 800 nm or less (mean particle size). In one embodiment the mean particle size is 200 to 1500 nm. In one embodiment the particles are 10 nm or more, or 50 nm or more, or 100 nm or more, or 300 nm or more, or 450 nm or more. In one embodiment the mean particle size is between 550-600 nm.

Figure 4A:
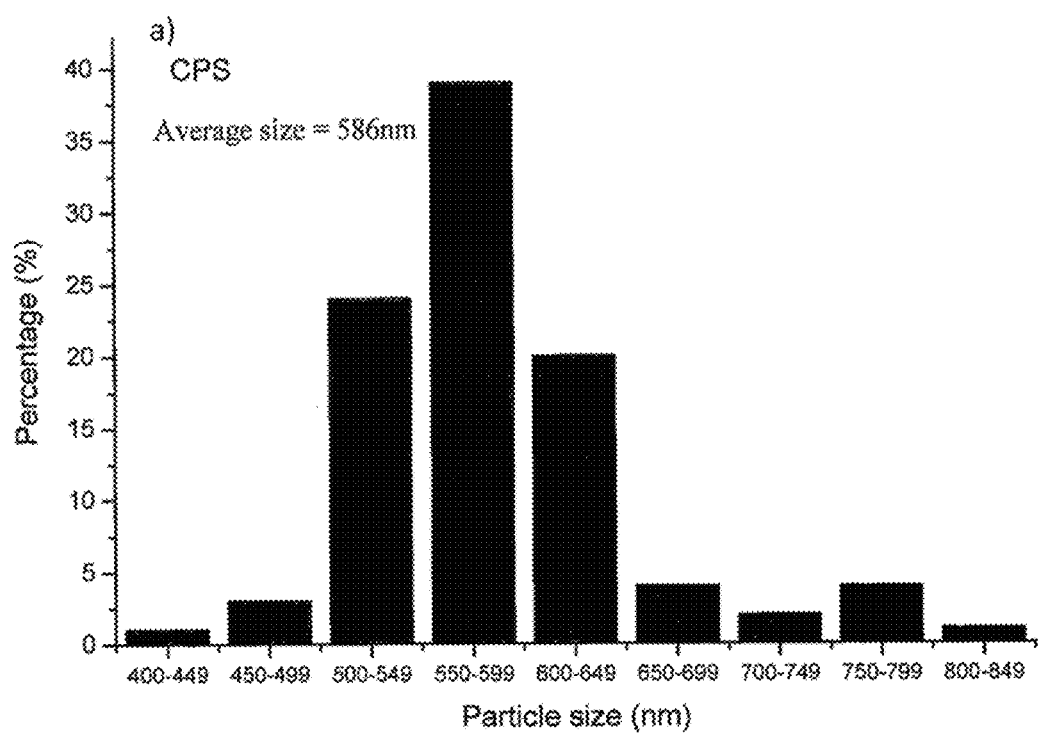
FIGS. 4A and 4B. Mean particle size of calcium phosphate particles according to the present invention, a) relates to particles not comprising strontium, b) relates to particles containing strontium.
Figure 4B:
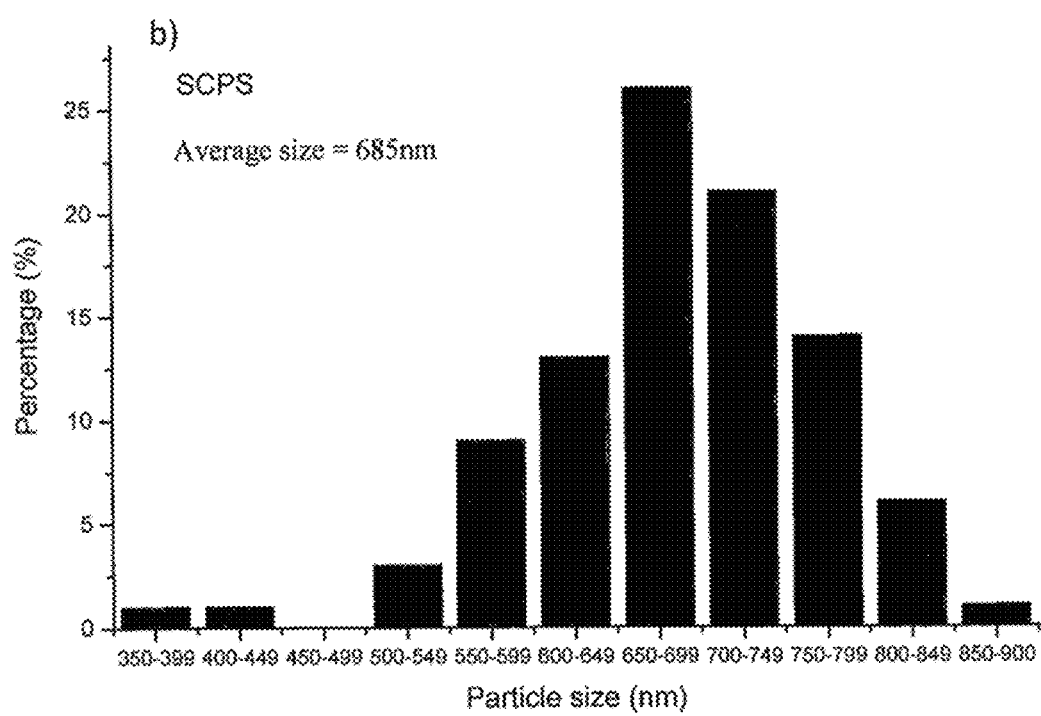
Figure 5:
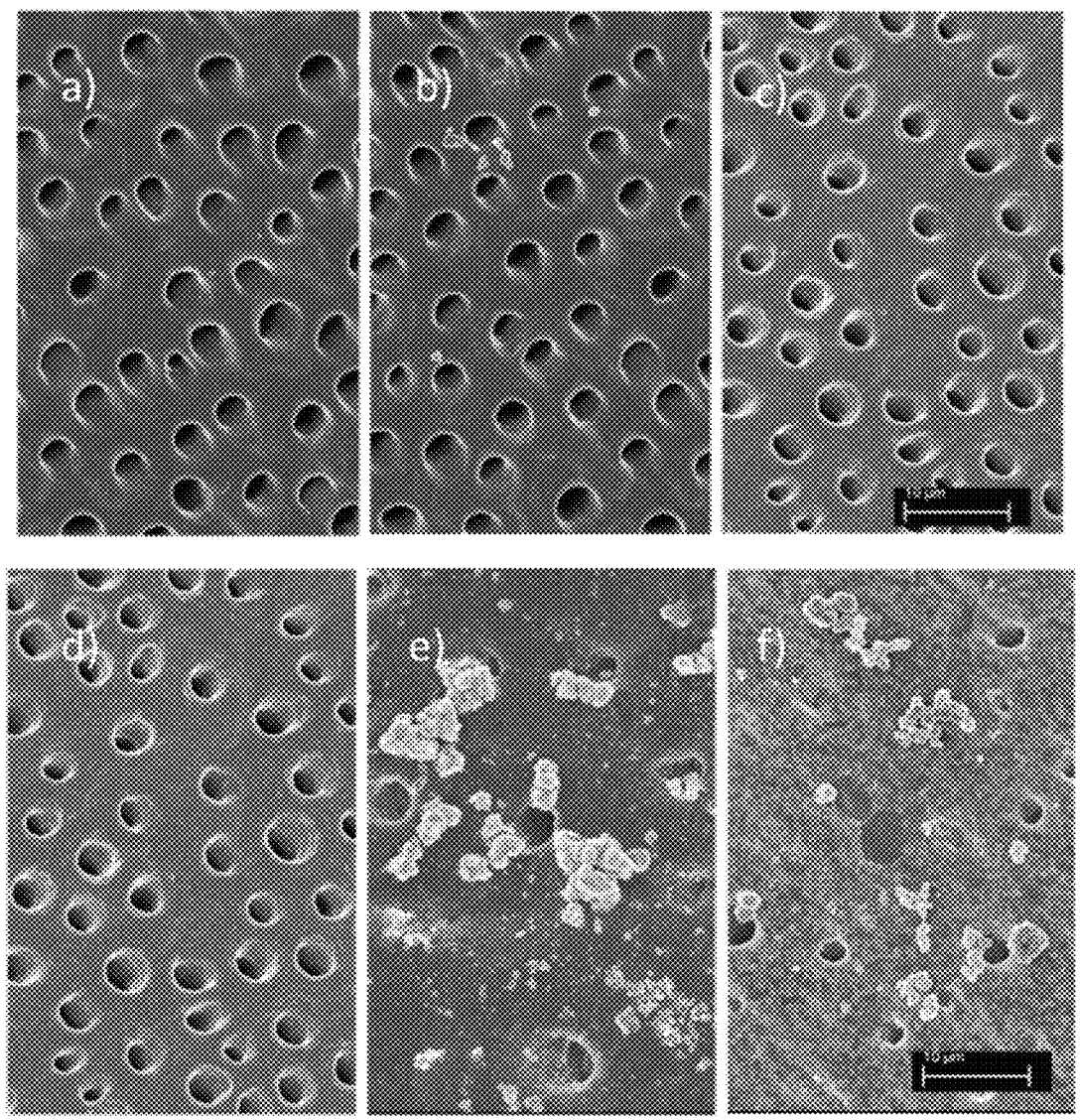
FIG. 5. SEM image. Tooth surfaces before brushing (a and d), after 3 days (b and e) and after 7 days (c and f)) for control (a-c) and paste comprising 1 weight % of SCPS (strontium containing calcium phosphate particles).
Figure 6:
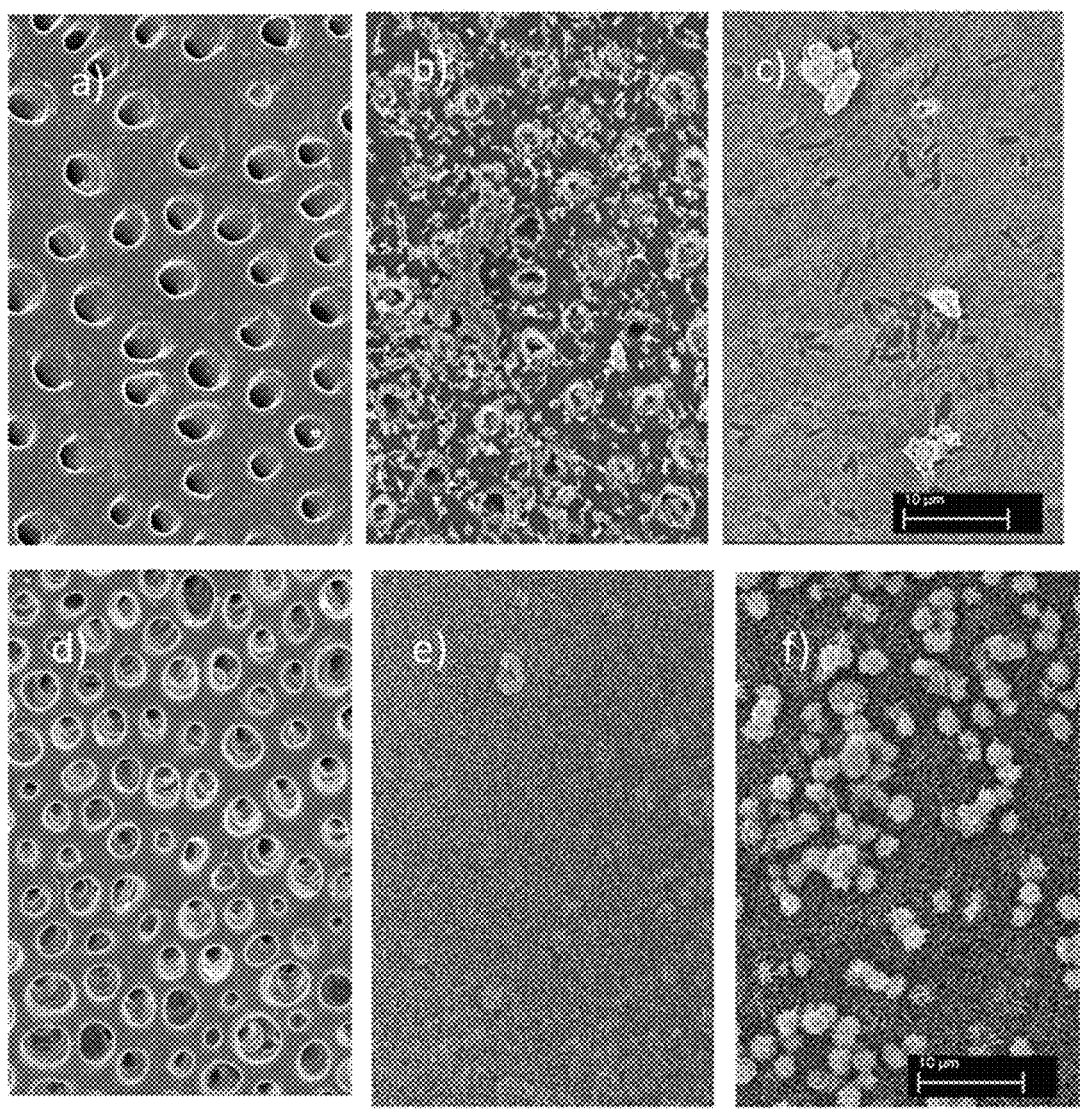
FIG. 6. SEM image. Tooth surfaces before brushing (a and d), after 3 days (b and e) and after 7 days (c and f)) for paste comprising 10 weight % SCPS (a-c) and tooth paste comprising 10 weight % of SCPS.
Figure 7:
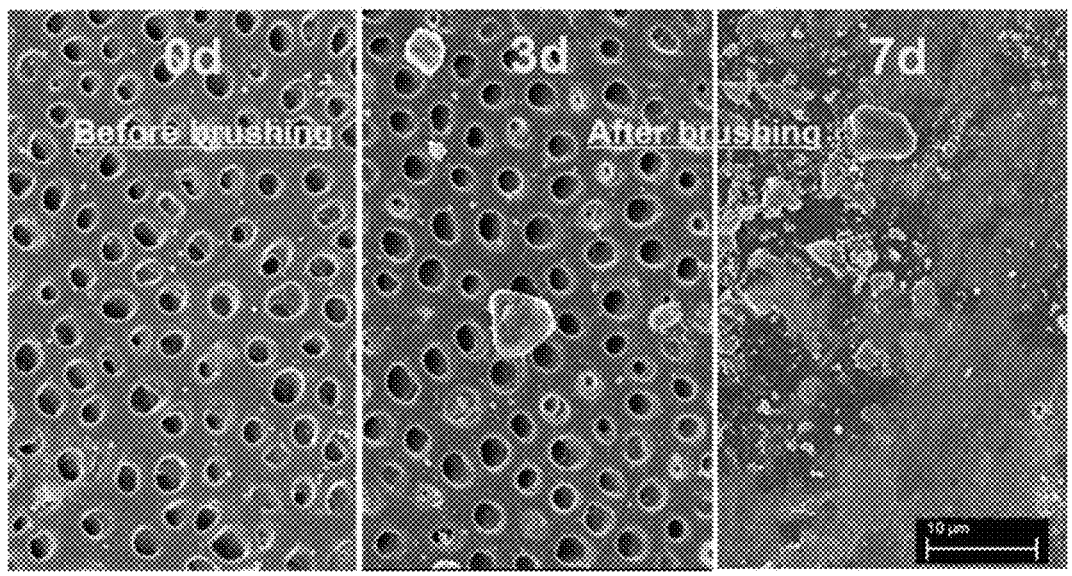
FIG. 7. SEM image. Tooth surfaces before brushing (a and d), after 3 days (b and e) and after 7 days (c and f)) for Sensodyne®.
Figure 8:
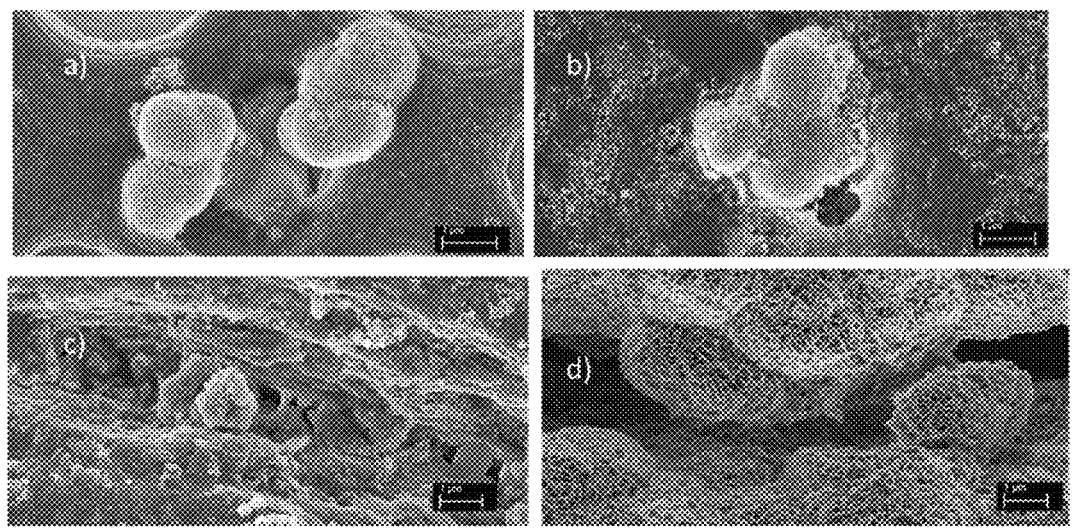
FIG. 8. SEM image. Tooth surface (a-b) and cross-section (c-d) of tooth treated with paste comprising 10 weight % SCPS, a) brushed once, b) 1 day, c) brushed once, and d) 7 days.
Figure 9:
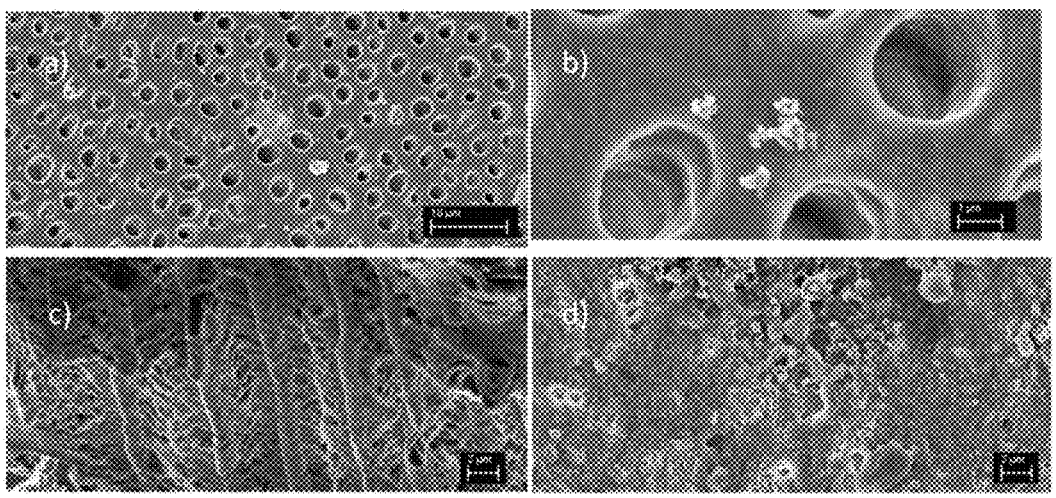
FIG. 9. SEM image. Tooth surface (a-b, d) and cross-section (c) of tooth brushed with Sensodyne®, a) brushed once, b) 1 day, c) 7 days, and d) 7 days. No or low remineralization.

In one embodiment more than 80% of the particles have a particle size between 450 to 700 nm. As can be seen in FIGS. 4A and 4B, the mean particle size is higher when strontium is used. Also, the size distribution is much wider when strontium is used. The mean particle size is determined by studying 100 particles using SEM (Scanning Electron Microscopy) and linear intercept method.

The particles of the present invention are hollow with an outer shell. The core part of the particles is preferably a void not comprising any calcium phosphate material. In one embodiment the shell of the particle is porous, in another embodiment the shell is dense. In one embodiment the thickness of the shell is 10-100 nm, for example 30-70 nm. In one embodiment the pores of the shell have an average pore size of up to 150 nm, for example 20-100 nm.

In one embodiment the particles have a hollow core and a shell and wherein the particle comprises 40-70 weight % of calcium, 20-40 weight % of phosphate and 1-25 weight % magnesium, and wherein the Ca/P weight ratio is in the range of 1.10 to 1.90, preferably 1.10 to 1.70, and wherein more than 80% of the particles have a particle size between 200 to 1500 nm, or preferably 450 to 700 nm, and wherein the particles are essentially free from strontium. FIGS. 28 to 36 clearly disclose particles according to the present invention having hollow cores (arrows pointing at hollow sections). One of way of studying the hollow structure of the obtained particles is by embedding the particles in a resin and polish them by hand in order to remove a part of the particle surface, see FIGS. 30A-C.

The crystallinity of the particles of the present invention may influence the remineralization of the teeth for example. The crystallinity may be at least 10%, preferably at least 50%, preferably at least 75%. The particles of the present invention are built from many small crystals.

It may be preferred that the obtained particles have at least partly the crystal structure and composition of hydroxyapatite. For example from a regulatory point of view it may be beneficial if the particles have the crystal structure and composition of hydroxyapatite. In one embodiment at least 10%, or at least 20%, or at least 30%, or at least 40%, or at least 50% of the crystal structure is that of hydroxyapatite as determined using Rietfeld refinement from XRD spectra. In one embodiment the particles according to the present invention have a hydroxyapatite crystallinity of 20 to 70%, for example 30 to 60%.

The particles of the present invention retain their morphology when kept at temperatures of up to 600° C.

The Method

The synthesis is performed in an aqueous buffer solution having a pH of 2-10, preferably a pH of 6-10, or pH 6-9, preferably 6.5 to 8 or more preferably a pH of 7.0-7.5, comprising calcium, phosphate, magnesium, potassium and sodium ions. The pH value of the solutions before and after precipitation is stable.

The concentration of calcium ions may be in the range of 0.1-5 mM, the concentration of magnesium ions may be in the range of 0.01-5 mM, and the concentration of phosphate ions can be in the range 1-10 mM. In one embodiment the calcium ion concentration is 0.1 to less than 2 mM, or 0.2 to 1 mM, and in another embodiment the magnesium ion concentration is 0.02 to 1 mM. In one embodiment the Ca:Mg molar ratio is from 1:3 to 4:1, for example 1:2 to 3:1, or 1:1 to 2:1.

The sodium (Na) and potassium (K) ions are believed to stabilize the buffer and acts as counter ions. These ions are therefore not expected to be found in the formed particles or at least not in any larger amounts. In the concentration of sodium ions in the solution is in the range of 0.01-1420 mM and the concentration of potassium ion is in the range of 0.01-1420 mM. The concentration of sodium may be 20 to 200 mM, or 30 to 150 mM, and the concentration of potassium ions may be 0.1 to 10, or 0.5 to 5 mM. The sodium ions may be added as NaCl or $Na_2HPO_4$ or as a combination, and potassium ions may be added as KCl or $KH_2PO_4$ or as combinations. In one embodiment the Na:K molar ratio is more than 23:1, preferably more than 30:1, more preferably more than 35:1. Preferably the buffer solution is essentially free from strontium ions, for example less than 0.01 mM, or less than 0.005 mM.

Without being bound by any theory it is believed that the presence of magnesium ions and the elevated temperature of the solution promotes the formation of a hollow structure.

In one embodiment the molar ratio of sodium:potassium:phosphate is 20-170:0.5-5:1-15. In another embodiment the molar ratio is 30-150:1-4:2-10. The molar ratio between Ca and P should be close to 1:10, for example 1:9.0 to 1:11, or 1:9.5 to 1:10.7, or 1:10 to 1:10.5.

Preferably, the buffer solution is prepared prior to the addition of the calcium and magnesium ions.

The buffer solution and the particles may further contain substitution ions. Potentially, cationic substitution ions are $Si^{4+}$, $Zn^{2+}$, $Ba^{2+}$, $Fe^{3+}$ or $Ti^{4+}$ and anionic substitution ions are $Cl^-$, $F^-$, $HCO_3^-$ or $CO_3^{2-}$. The source for the ion substitutions can be soluble salts and slightly-soluble salts containing the ions to be substituted, such as but not limited to $Na_2SiO_3$, calcium silicates such as ($CaOSiO_2$, $CaO(SiO_2)_2$, $CaO(SiO_2)_3$); $ZnCl_2$, $ZnSO_4$, $BaCl_2$, $FeCl_3$, $Fe(NO_3)_3$, $Na_2CO_3$, NaF, $Na_2FPO_4NaHCO_3$ or $NaTiO_3$. In one embodiment the buffer solution does not contain strontium.

The water used to prepare the aqueous buffer solution should be purified water. The water may be deionized, distilled, double distilled or ultra-pure water. For example the water may be Milli-Q®.

As mentioned above, the method of the present invention is temperature driven which means that if the temperature is too low, spheres and especially hollow spheres will not be formed or at least not formed within a reasonable period of time. The temperature in the present invention is at least 60° C., or at least 70° C., or at least 80° C. The temperature may be 90° C. or more, 100° C. or more, or 200° C. or less, or 150° C. or less. A preferred temperature range is from about 60° C. to 170° C., or 70° C. to 150° C., or from about 80° C. to 120° C. The method could be a static process, stirring or shaking process or a hydrothermal process.

The particles may be isolated using any suitable technique for example filtering, evaporation, centrifugation or combinations thereof. The size distribution disclosed in FIGS. 4A and 4B is obtained after filtering using a filter that allows particles of 100 nm and less to pass through. In other words the method of the present invention itself results in the size distribution seen in FIGS. 4A and 4B, the filtering process is more or less only used to remove water.

The method of the present invention facilitates a very short synthesis time but it is also believed that time will influence the particle size distribution. The synthesis time may be 1 minute, but it may be a couple of hours. In one embodiment the synthesis time is at least 2 minutes, or at least 5 minutes, or at least 10 minutes, or at least 30 minutes, or at least 1 hour, or at least 2 hours, or at least 6 hours, or at least 20 hours. The obtained particles will have essentially a TCP structure, such as β-TCP. In one embodiment the method comprises heating at 60 to 200° C. for at least 5 minutes;

The crystal structure and composition of hydroxyapatite may be obtained by an additional method step. By placing the obtained spherical hollow particles, optionally also washed, in a solution comprising calcium ions for a suitable period of time, for example at least 1 hour, or at least 3 hours, or at least 7 hours, or at least 12 hours, the obtained particles will have hydroxyapatite structure. In one embodiment the suitable period of time is 10-24 hours. The spherical hollow particles will then form at least partly hydroxyapatite crystal structure, for example if the crystal structure of the obtained hollow particles is mainly β-TCP the particles will after this treatment contain at least partly hydroxyapatite crystal structure and composition. It is a diffusion process where the calcium ions diffuse into the pre-formed particles and alters the crystal structure.

The solution of calcium ions of the additional step may have calcium salt concentration of 0.1-1.0M and non-limiting examples of salts are calcium nitrate and calcium chloride. The process time is temperature dependent and decreases with increasing temperature. The solution may be heated preferably to a temperature of at least 60° C., or at least 70° C. In one embodiment the temperature is from 60° C. to 150° C. In another embodiment the temperature is from 80° C. to 120° C. The obtained particles may then be separated using any suitable technique and washed using any suitable solvent for example alcohol.

In order to increase the crystallinity the formed particles may be heat treated. In one embodiment the particles are treated during at least 30 minutes at a temperature of at least 100° C. In another embodiment the particles are autoclaved, for example at 80° C. or more, or 100° C. or more. In another embodiment the particles are treated during at least 1 hour at a temperature of at least 300° C. Higher crystallinity decreases the solubility of the particle which may be beneficial in certain applications, for example when used in an implant, as a void filler or where ever the particles are needed for a longer period of time. Many calcium phosphate materials used today are totally amorphous or have a very low degree of crystallinity. The present invention presents a method that result in highly crystalline particles.

Applications

The particles of the present invention may be used as a bleaching agent or paste. A problem with prior art has been that the bleaching also degrade the enamel resulting in increased sensitivity of the tooth gingival irritation. The present invention aims at delivering a bleaching agent locally using the particles of the present invention which will remineralize the tooth during and/or after the bleaching step. The preparation of a bleaching agent with the particles of the present invention comprises:

providing particles of the present invention and a solution of a bleaching additive for example a peroxide solution;

mixing the particles and the solution, for example peroxide solution; and isolating the bleaching additive containing particles.

The peroxide used may be hydrogen peroxide or carbamide peroxide or a mixture thereof. Other non-limiting examples of tooth bleaching additives include; sodium percarbonate, sodium chlorite, sodium perborate, peroxymonosulphate, peroxide plus metal catalysts and oxireductase enzymes. The concentrations of peroxides in the solution may be 0.1-60 wt % such as 1 wt % or more, or 5 wt % or more, or 10 wt % or more or 15 wt % or more, or 20 wt % or more, or 25 wt % or more, but 55 wt % or less, or 50 wt % or less, or 45 wt % or less, or 40 wt % or less. For example the concentration may be 10-60 wt % for carbamide peroxide, and 0.1-35 wt % for example for hydrogen peroxide such as 10-35 wt % for hydrogen peroxide.

In one embodiment the mixing continues for a few seconds, or for 1 minute to 3 hours, or for 10 minutes to 2 hours. The isolated particles may be washed or rinsed using any suitable solvent, for example water.

The preparation of bleaching pastes comprises:
providing a bleaching agent as described above and a paste forming compound; and
mixing the agent and the paste forming compound.

The paste forming compound/bleaching agent weight ratio may be 100:1 to 1:5, such as 20:1 to 1:4, or 5:1 to 1:3, or 2:1 to 1:2, or 1:2 to 1:5. In one embodiment the concentration of bleaching additive in the paste is 0.1-35 wt %, for example 1 wt % or more, or 10 wt % or more, or 35 wt % or less, or 25 wt % or less, or 15 wt % or less. In one embodiment the paste forming compound is glycerol. The paste may also be free from water or at least essentially free from water or at least less than 2 wt %, or preferably less than 1 wt %, or more preferably less than 0.5 wt % or even more preferably less than 0.1 wt %.

In one embodiment the bleaching agent is delivered in a two-compartment system where a paste containing pre-loaded spheres (e.g. carbamide peroxide loaded) and glycerol is arranged in one compartment and a second paste is containing water based hydrogen peroxide is arranged in the second compartment. The two pastes can then be mixed when applied to the tooth surface via a mixing tip for example.

Figure 18:
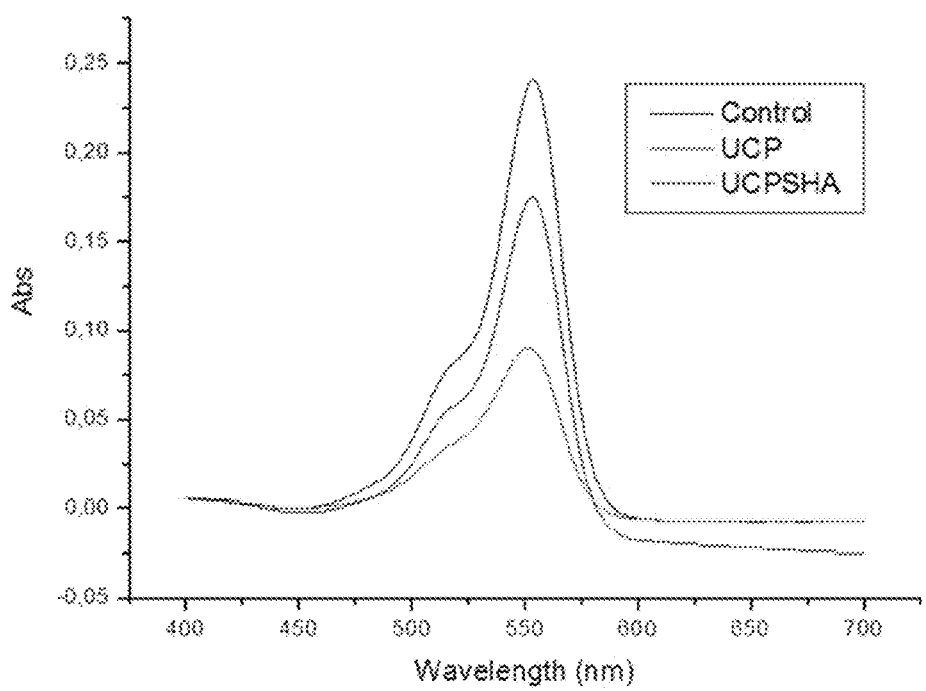
FIG. 18. Absorbance measurements to determine the load and release of peroxide from the particles of the present invention (SCPS) in a solution comprising Rhodamine B.
Figure 19:
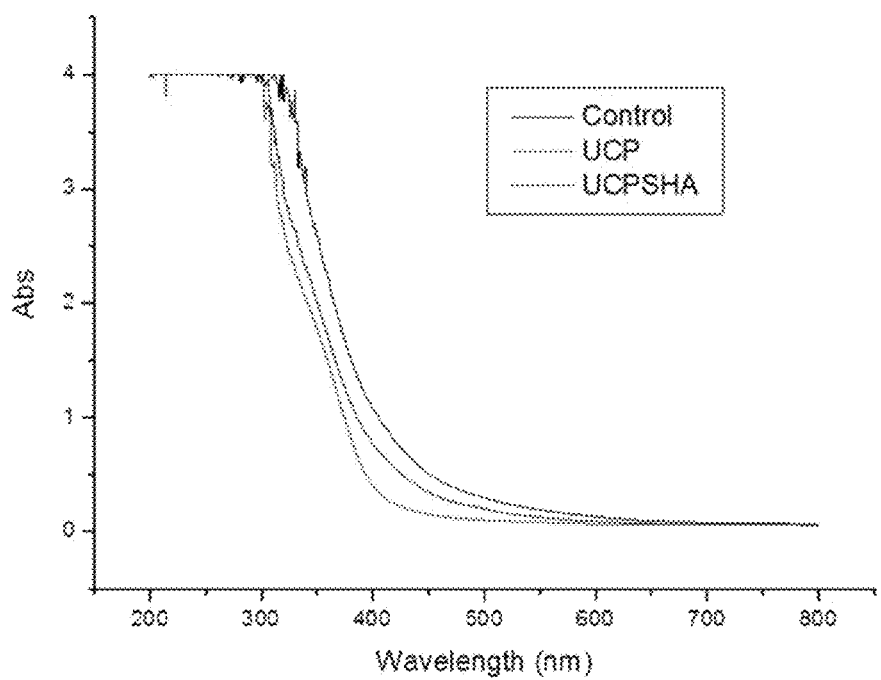
FIG. 19. Absorbance measurements to determine the load and release of peroxide from the particles of the present invention (SCPS) in a solution comprising yellow tea solution.
Figure 20:
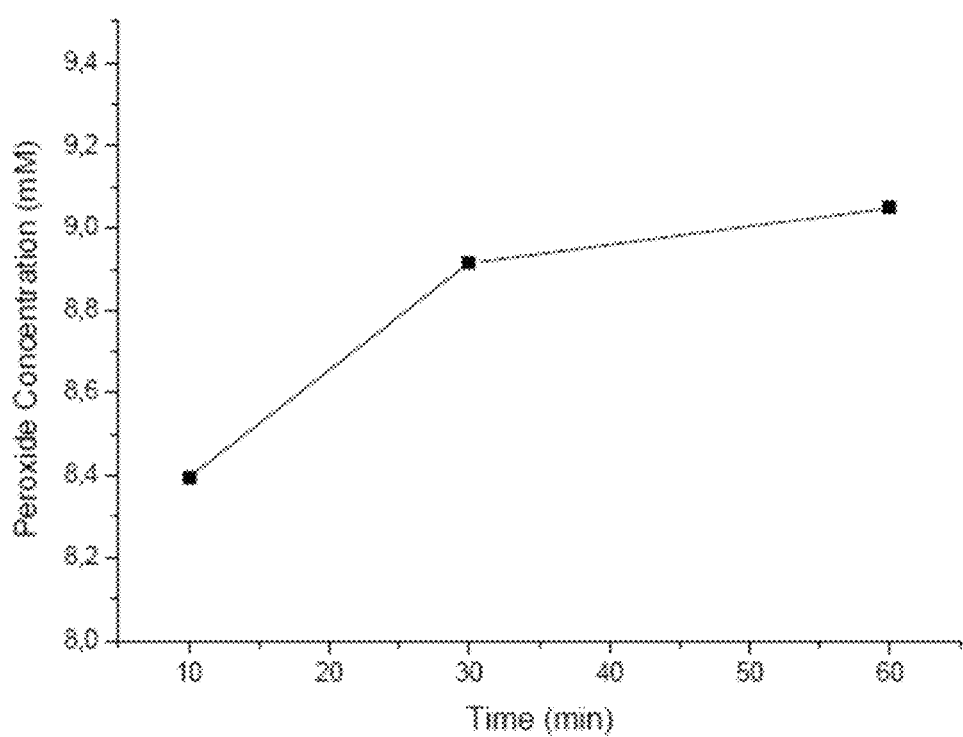
FIG. 20. Release curve for peroxide from particles according to the present invention.

As can be seen in FIGS. 18 and 19 the particles of the present invention are suitable for loading and releasing bleaching additives. This is most likely due to the hollow and porous morphology of the particles. FIG. 20 shows also the release curve for loaded particles where after an initial burst release a sustained release is shown. The particles of the present invention facilitates a sustained release of bleaching additive which makes it possible to use lower amount of said additive since the effect of it is prolonged.

The bleaching agent or paste may be added to the discolored teeth where the bleaching additive may be released and the particles will start to remineralize the teeth.

The present invention may be used to prepare a tooth paste. The tooth paste may be prepared by
providing particles of the present invention, preferably as a bleaching agent or paste as described above, a paste forming compound, and a surfactant; and
mixing said components.

In one embodiment the composition according to the present invention the amount of spherical particles is at least 0.5 wt %, preferably at least 1 wt %, or at least 5 wt %, or at least 10 wt %. For example the tooth paste may comprise 0.5-50 wt % of particles, for example 1 weight % or more, or 3 weight % or more, or 5 weight % or more, or 7 weight % or more, or 10 weight % or more, or 50 weight % or less, or 30 weight % or less, or 20 weight % or less, or 15 weight % or less. As a paste forming compound may polyethylene glycol, polyvinyl alcohol or polysaccharides such as cellulose such as sodium cellulose, hyaluronan, chitosan or glycerol or a mixture thereof be used. The paste may also contain water, for example 0.1 to 5 weight %, however in one embodiment the paste is essentially free from water. In one embodiment the composition does not contain water. The reason for limiting the amount of water is that the particles will degrade if stored for longer periods of time in water. The paste may contain additional glycerol and optionally also a sweetener such as sorbitol. The paste may further comprise NaF and/or sodium benzoate. The tooth paste may be good for tooth anti-sensitivity and remineralization. In one embodiment the tooth paste comprises: 12% of particles of the present invention, 2% or sodium cellulose, 40% glycerol, 10% sorbitol, 1% sodium lauryl sulphate, 0.1% NaF, 0.1% sodium benzoate and 34.8% water.

The particles of the present invention may also be used as an implant material or as bone void filler. The particles or the composition of the present invention have shown great potential for filling cavities such as dental tubuli and also remineralization and therefore the present invention is suitable for bone void filling material or treatments of exposed dental tubuli and remineralization of teeth or bone, see table 1. The size of the particles facilitates that they may enter dental tubuli or other cavities and without being bound by theory it is believed that the size of the particles also makes the particles stick to the teeth and thereby stays longer at the treatment site making the particles and the composition more efficient. Too small particles are however very hard to handle and to make a paste that is easy to handle. The hollow morphology makes it possible to load the particles with active substances and it also makes the particles light. The particles according to the present invention may therefore be used as drug/gene delivery vehicles.

TABLE 1

Remineralization of teeth using composition of the present invention in comparison with Sensodyne ® and Colgate ®

| Composition | 3 days | 7 days |
| --- | --- | --- |
| *Paste with 0.5 weight % CPS | Partly remineralized | Partly remineralized |
| *Paste with 1 weight % CPS | Partly remineralized | Totally remineralized |
| *Paste with 5 weight % CPS | Totally remineralized | Totally remineralized |
| *Paste with 10 weight % CPS | Totally remineralized | Totally remineralized |
| **Paste with 1 weight % SCPS | Partly remineralized | Partly remineralized |
| Paste with 10 weight % SCPS | Almost fully remineralized | Totally remineralized |
| ***Tooth paste with 12 weight % SCPS | Totally remineralized | Totally remineralized |
| Sensodyne ® | Some particles on the surface | Partly remineralized |
| Colgate ® | Some particles on the surface | Partly remineralized |

*Paste with cellulose and Calcium Phosphate particles without Sr (CPS)
**Paste with glycerol and Strontium containing Phosphate particles SCPS
***Paste with 2% or sodium cellulose, 40% glycerol, 10% sorbitol, 1% sodium lauryl sulphate, 0.1% NaF, 0.1% sodium benzoate and 34.8% water and SCPS

EXAMPLES

Example 1

Preparation: NaCl, KCl, $Na_2HPO_4$ and $KH_2PO_4$ are dissolved in water by the molar ratio of 137.0:2.7:8.1:1.5 to form the phosphate buffer solution (pH 7.4). Then calcium (1 mM) and magnesium (0.5 mM) salts, such as chlorides, are dissolved in the solution. The as-prepared buffer solution is heated at 80° C. under stirring. After 6 hours, the precipitation is filtered and washed by ethanol for twice. The crystallinity, composition, and morphology are analyzed by XRD, EDS and SEM, separately.

TABLE 2

Ca, P and Mg contents in the particles analysed by EDS.

| Ion | wt % |
| --- | --- |
| Ca | 60.9 |
| P | 32.9 |
| Mg | 6.2 |
| Ca/P | 1.43 |

Example 2

Preparation: NaCl, KCl, $Na_2HPO_4$ and $KH_2PO_4$ are dissolved in water by the molar ratio of 63.5:1.4:4.1:0.7 to form the phosphate buffer solution (pH 7.4). Then calcium (0.5 mM) and magnesium (0.3 mM) salts, such as chlorides, are dissolved in the solution. The as-prepared buffer solution is heated at 80° C. under stirring. After 6 hours, the precipitation is filtered and washed by ethanol for twice.

Example 3

Preparation: NaCl, KCl, $Na_2HPO_4$ and $KH_2PO_4$ are dissolved in water by the molar ratio of 31.8:0.7:2.1:0.4 to form the phosphate buffer solution (pH 7.4). Then calcium (0.25 mM) and magnesium (0.15 mM) salts, such as chlorides, are dissolved in the solution. The as-prepared buffer solution is heated at 80° C. under stirring. After 6 hours, the precipitation is filtered and washed by ethanol for twice.

Example 4

Preparation: NaCl, KCl, $Na_2HPO_4$ and $KH_2PO_4$ are dissolved in water by the molar ratio of 44.3:0.9:2.7:0.5 to form the phosphate buffer solution (pH 7.4). Then calcium (0.34 mM) and magnesium (0.13 mM) salts, such as chlorides, are dissolved in the solution. The as-prepared buffer solution is heated at 80° C. under stirring. After 6 hours, the precipitation is filtered and washed by ethanol for twice.

Example 5

Preparation: NaCl, KCl, $Na_2HPO_4$ and $KH_2PO_4$ are dissolved in water by the molar ratio of 137.0:2.7:8.1:1.5 to form the phosphate buffer solution (pH 7.4). Then calcium (1 mM) and magnesium (0.02-0.4 mM) salts, such as chlorides, are dissolved in the solution. The as-prepared buffer solution is heated at 80° C. under stirring. After 6 hours, the precipitation is filtered and washed by ethanol for twice.

Example 6

Four different pastes were prepared to study remineralization of teeth and dental tubuli. One paste (control) comprised cellulose and water, one paste comprised glycerol together with 1 weight % of strontium containing particles (SCPS), one paste comprised glycerol and 10 weight % of SCPS and one paste comprised 12% of SCPS, 2% or sodium cellulose, 40% glycerol, 10% sorbitol, 1% sodium lauryl sulphate, 0.1% NaF, 0.1% sodium benzoate and 34.8% water (denoted Tooth paste).

A comparison study was done also with Sensodyne® which contains bioglass.

Human teeth were cut into slabs. Each slab was brushed with the pastes using a tooth brush for 3 minutes and then rinsed with tap water for approximately 30 seconds to remove residues. The samples were then placed in a 37° C. simulated saliva for 3 hours. The process was repeated three times a day for one week.

FIGS. 5 to 9 show that the control does not show any effect while paste with 1 weight % SCPS shows already after 3 days remineralization and after 7 days almost the whole surface have been remineralized. Both the paste and the "tooth paste" containing 10 weight % SCPS showed a very fast remineralization. After just 3 days almost the whole surface was covered and remineralized. The cross-section FIGS. 8 c-d disclose that the particles have entered into the dental tubuli and remineralized said tubuli.

In comparison, Sensodyne® did not show at all the same effect. Even after a week no clear remineralization could be seen. The large particles visible in the figures are believed to be the bio glass, FIGS. 7 and 9.

Figure 10:
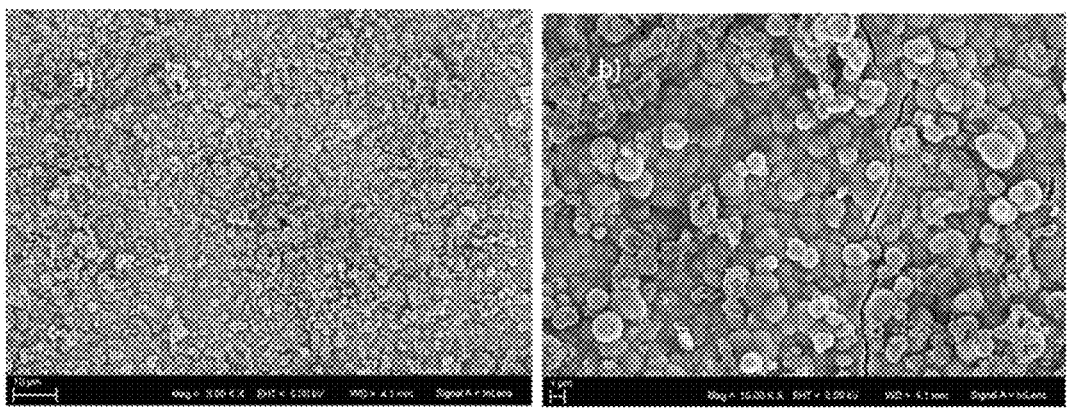
FIG. 10. SEM image. Remineralized surface with adhered SCPS particles.
Figure 11:
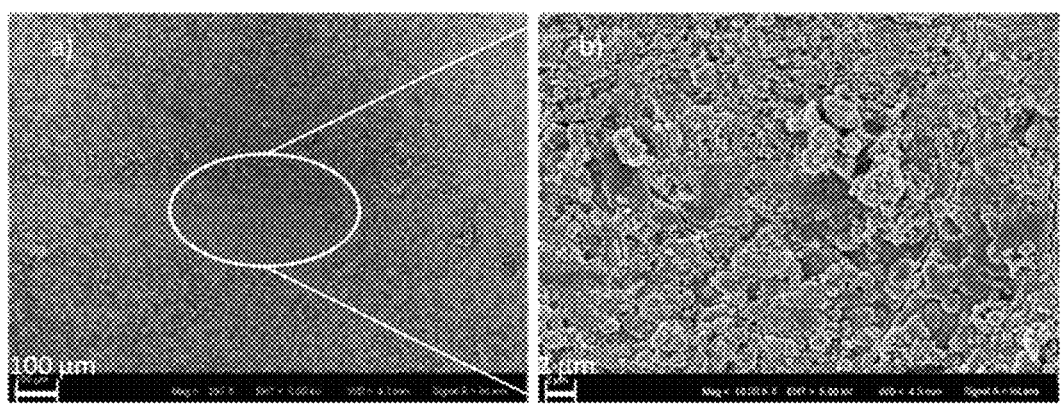
FIG. 11. SEM image. Remineralized surface that has been scratched, in a) is the site of scratched seen and in b) is the magnification of the scratch site.

FIGS. 10 and 11 also disclose that the remineralized surface allows the particles to adhere to allow further remineralization and the surface is resistant to scratches.

Table 1 discloses the results also in comparison with CPS.

Example 7

To test how well the remineralized surfaces withstand acid environment tooth plates that had been brushed for two weeks were used. To different buffer solutions were used, on having a pH of 2.5 (similar to an ordinary carbonated soft drink) and one having a pH of 6. The tooth plates were placed in the solutions for 30 seconds and 2 minutes.

Figure 12:
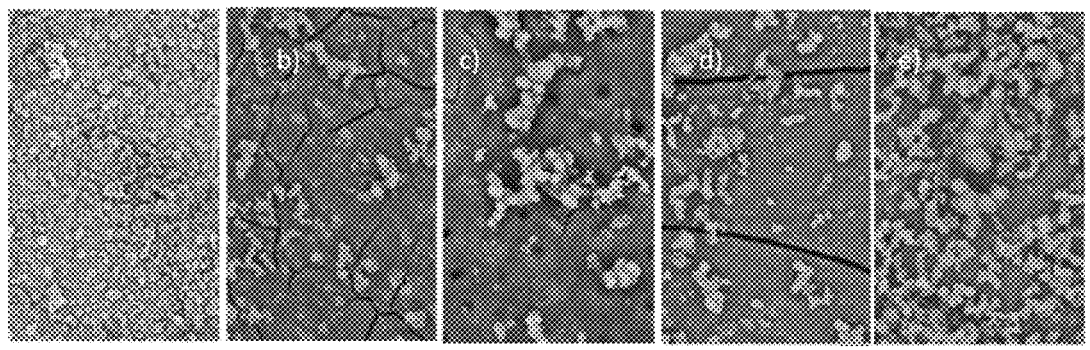
FIG. 12. SEM image. Remineralized surface exposed to acidic solution, a) before soaking in acidic solution, b) 30 s in pH 2.5, c) 2 min. in pH 2.5, d) 30 s in pH 6 and e) 2 min. in pH 6.

FIGS. 12 b and c. After 30 seconds in pH 2.5 the surface was still covered by mineralized CaP. After 2 minutes some dental tubuli could be observed but still a large part of the surface was still mineralized.

FIGS. 12 d and e. After both 30 second and 2 minutes in pH 6 the surface was still covered by mineralized CaP.

Example 8

Pastes comprising glycerol and 0.5, 1, 5 and 10 weight % particles not comprising strontium (CPS) were prepared. Human teeth were cut into slabs. Each slab was brushed with the paste using a tooth brush for 3 minutes and then rinsed with tap water for approximately 30 seconds to remove residues. The samples were then placed in a 37° C. simulated saliva for 3 hours. The process was repeated three times a day for one week.

Figure 13:
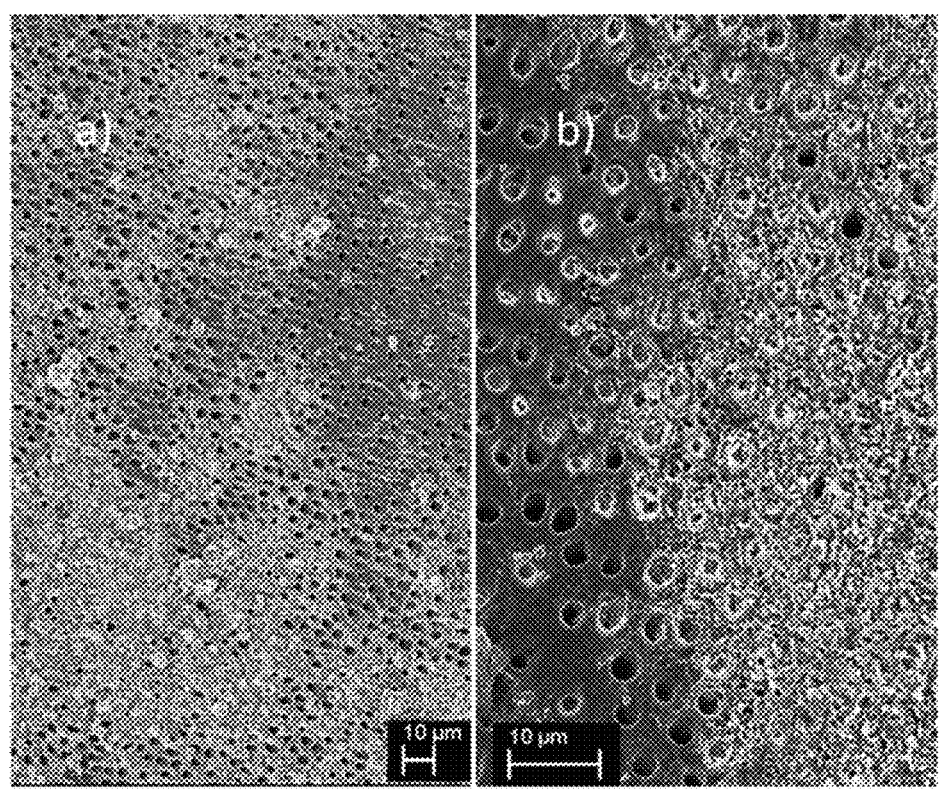
FIG. 13. SEM image. Tooth surface after treatment with a paste comprising 0.5 weight % CPS for 3 and 7 days respectively, a) and b) respectively.
Figure 14:
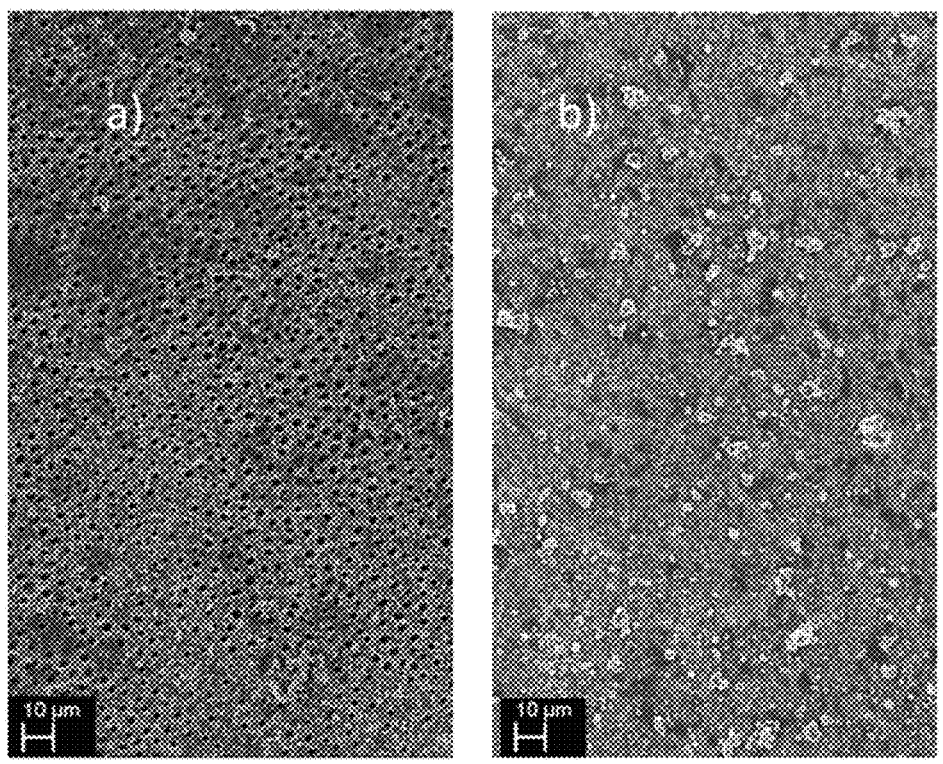
FIG. 14. SEM image. Tooth surface after treatment with a paste comprising 1 weight % CPS for 3 and 7 days respectively, a) and b) respectively. The surface is partly covered after 3 days but after 7 days the surface is totally covered.
Figure 15:
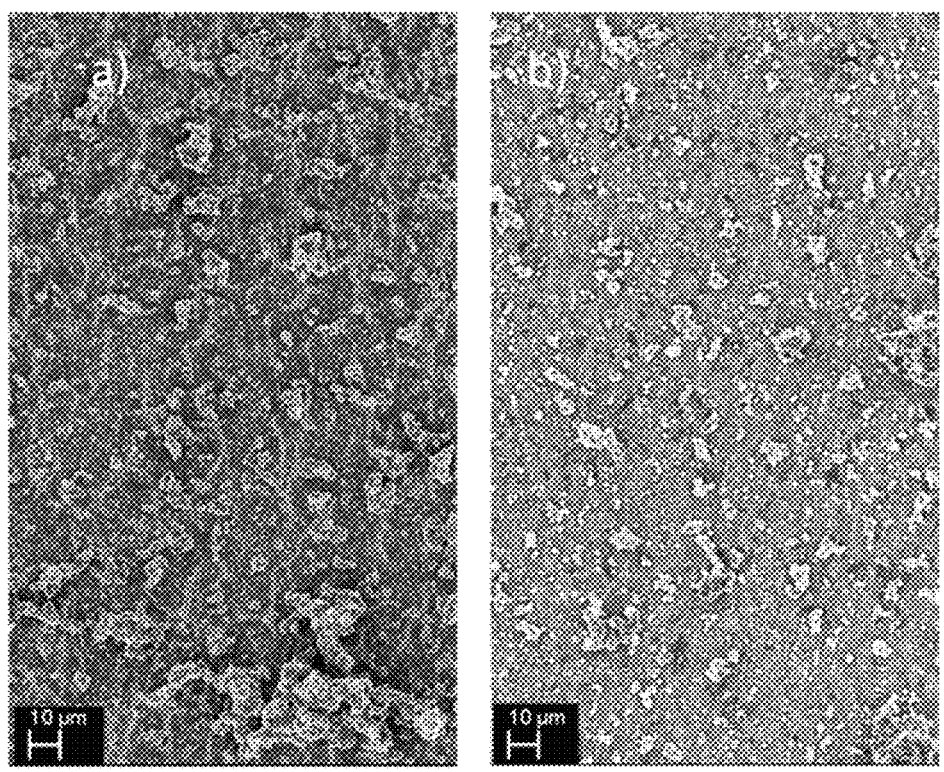
FIG. 15. SEM image. Tooth surface after treatment with a paste comprising 5 weight % CPS for 3 and 7 days respectively, a) and b) respectively. The surface and the exposed tubuli have been fully covered after 3 days and also after 7 days the surface is totally covered.
Figure 16:
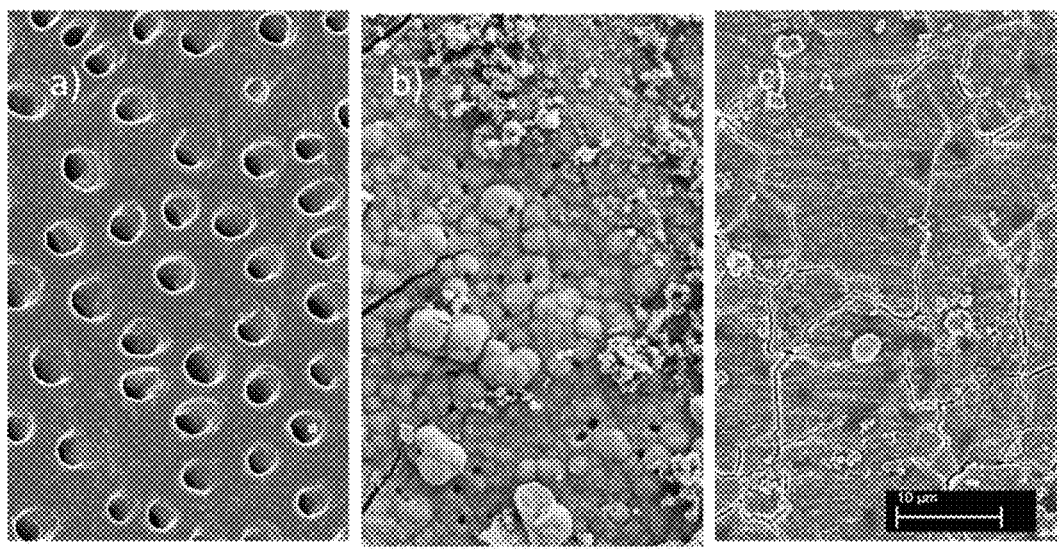
FIG. 16. SEM image. Tooth surface after treatment with a paste comprising 5 weight % CPS a) before brushing, b) after 3 and c) 7 days respectively. The surface and the exposed tubuli have been fully covered after 3 days and also after 7 days the surface is totally covered and remineralized.
Figure 17:
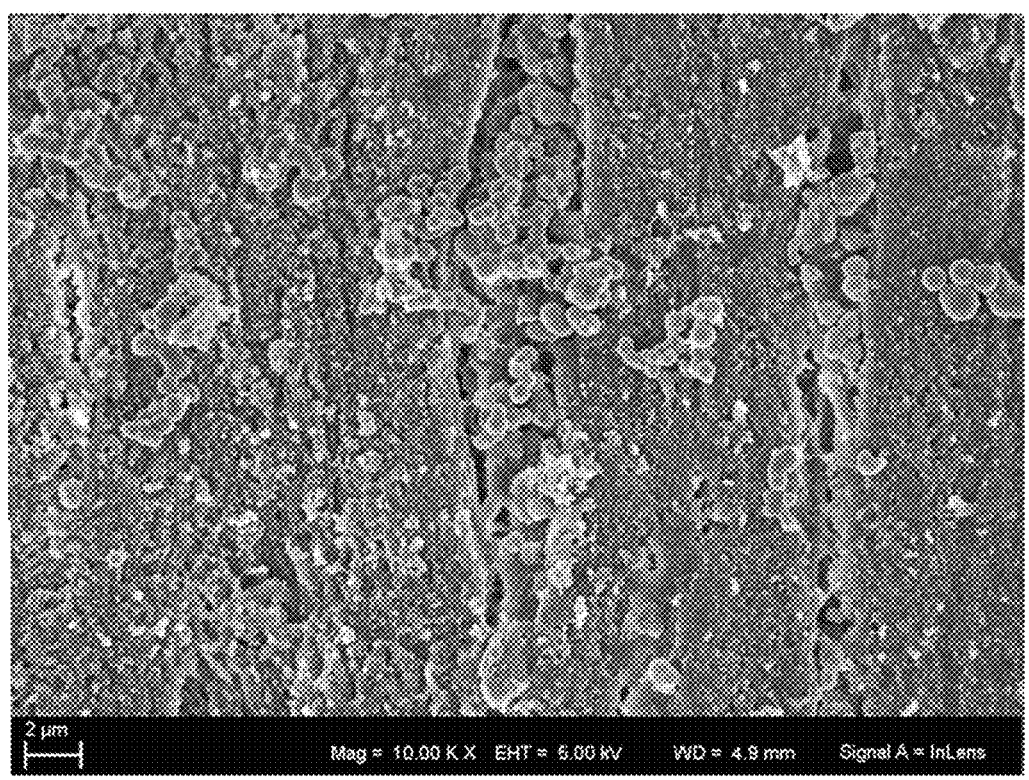
FIG. 17. SEM image. Cross-section of a tooth showing the dental tubuli filled with particles according to the present invention. The exposed tubuli has also been remineralized.

The paste comprising 0.5 weight % showed that after 7 days the surface was partly covered by particles and some remineralization could be seen, see FIG. 13. The paste comprising 1 weight % showed after 3 days a lot of particles on the surface and after 7 days the surface was completely covered, FIG. 14. The paste comprising 5 weight % resulted in a completely covered surface already after 3 days, FIG. 15. The paste comprising 10 weight % resulted in a surface which was completely covered and remineralized already after 3 days, FIG. 16. The particles also entered into the dental tubuli and remineralized said tubuli, FIG. 17.

Table 1 discloses the results also in comparison with Sensodyne®, Colgate® and SCPS.

Example 9

Materials
(1) Testing solutions: Rhodamine B and Yellow tea solutions
(2) Groups: Control, carbamide peroxide (UCP), UCP loaded SCPS spheres (UCP@SCPS)

Methods (1) UCP loading: 0.2 g of SCPS powder was immersed into 5 ml of 10% wt UCP solution with stirring for 3 hours, and then was centrifuged, cleaned and dried at 37° C.

(2) Bleaching: (in an oven at 37° C. for 24 hours)

Control: 3 ml of dye (Rho and yellow tea solutions) in a glass beaker cover by a parafilm UCP: 0.05 g of UCP was put into 3 ml of dye in a glass beaker cover by a parafilm UCP@ SCPS: 0.05 g of UCP@SHA was put into 3 ml of dye in a glass beaker cover by a parafilm Results The absorbance of the Rho and tea solutions decreased after the solutions have been mixed with UCP@ SCPS powder. That means UCP could be loaded in the SCPS, and then released. See FIGS. 18 and 19

(1) Temperature will affect the bleaching effect. The higher temperature is better.
(2) UCP@SHA powder is sticky because the UCP is like a wet powder.

Example 10

Peroxide Release from Particles

Particles were loaded with carbamide peroxide (CP). The loaded particles were mixed with PBS (pH 7.4) at a ratio of 1:10. The release of peroxide was determined using chemiluminescence. 8-10 samples per groups were used.

The results showed an initial burst effect but then a slow release, see FIG. 20.

Example 11

Teeth were tea-stained for up to 10 days before testing. The baseline shade [L] was determined for each tooth individually using Easy Shade.

Two different bleaching pastes were prepared and tested. The first was a water based paste with particles of the present invention loaded peroxide ($H_2O_2$) the peroxide concentration in the paste was 20 wt % (Psilox 20%) and as control was a commercial product with 36 wt % peroxide ($H_2O_2$) used. The second was a water-free paste with particles of the present invention loaded peroxide ($H_2O_2$) with a peroxide ($H_2O_2$) concentration of 3 wt % (Psilox 3%) as control were strips with 10 wt % peroxide ($H_2O_2$) used.

Psilox 20% was tested during 45 minutes exposure followed by washing and then storage at room temperature and follow-up measurement of [L] after 10 minutes and 24 h. The control was applied three times with 15 minutes between each application [L] was determined after 45 minutes.

Psilox 3% was tested during 45 minutes exposure followed by washing and then storage at room temperature and follow-up measurement of [L] after 2 hours. The control (the strip) was applied according to the IFU (2*30 minutes exposure).

Data is presented as change in [L] between each measurement. The surfaces were studied using SEM to determine eventual adhesion of spheres to the surface, pictures were taken after each measurement.

| Test | Result, change in [L] |
| --- | --- |
| Control (36%) | 22.3 |
| Psilox 20% | 11.5 |
| Psilox 20%, 10 min after | 14.5 |
| Psilox 20%, 24 hours after | 20.0 |
| Control strip (10%) | 6.7 |
| Psilox 3% | 9.1 |
| Psilox 3%, after 2 hours | 8.9 |

Figure 21:
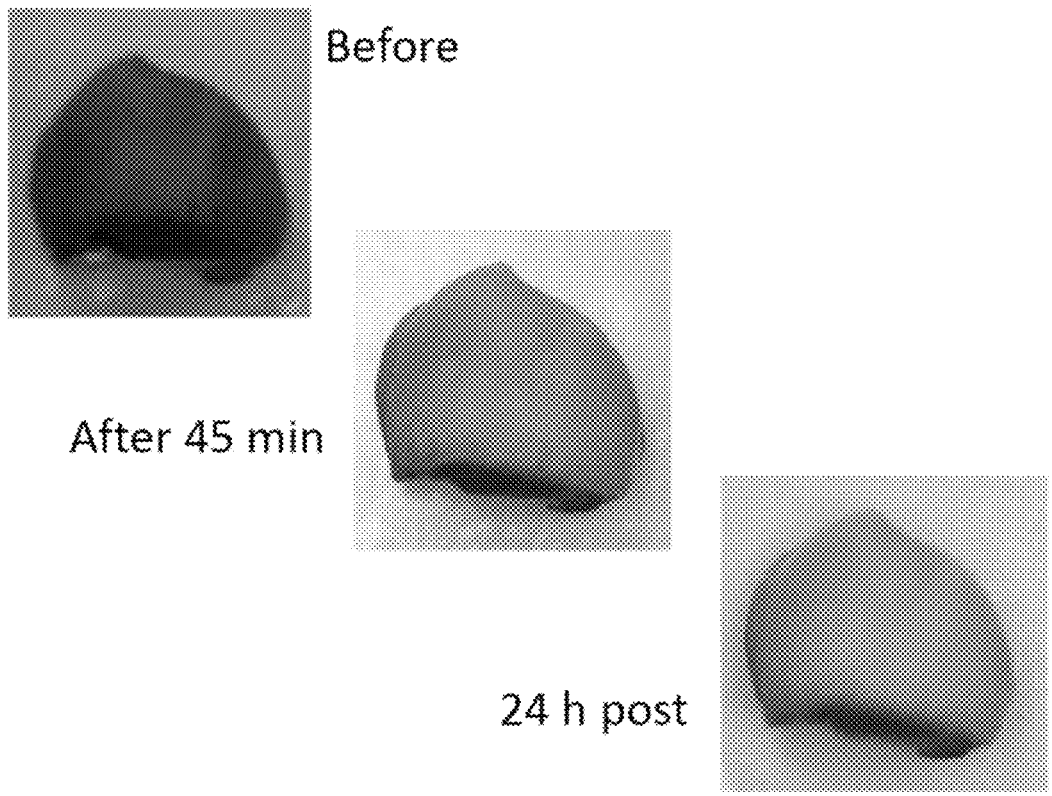
FIG. 21. Photos of tooth before and after bleaching, 45 minutes and 24 hours.

The control bleached 6-8 shades while Psilox 20% bleached around half after 45 minutes and almost as much as the control after 24 hours this by using much less amount of peroxide, see FIG. 21. This also shows that the present invention allows for continued bleaching through continued release of the particles that adhere to the surface.

The Psilox 3% bleached more than the control after shorter exposure time and with lower amount of peroxide.

Figure 22:
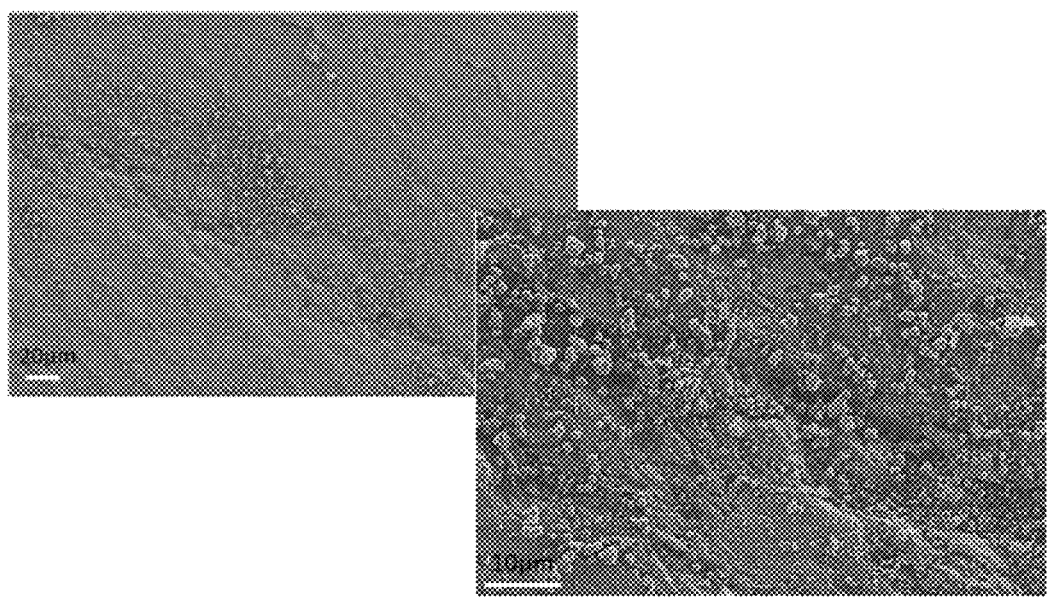
FIG. 22. SEM pictures disclosing the enamel surface with particles adhered thereto.

SEM pictures confirmed that the particles adhered to the enamel surface, see FIG. 22.

Example 12

Figure 23:
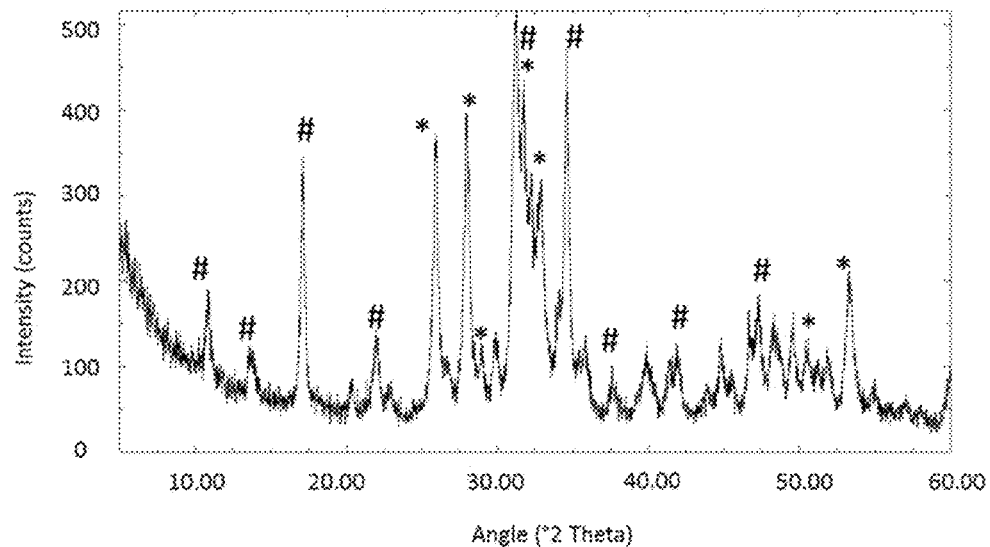
FIG. 23. XRD pattern of spheres after treated at 110° C. for 24 hours in Ca solution (*: hydroxyapatite, #: beta-TCP).
Figure 24:
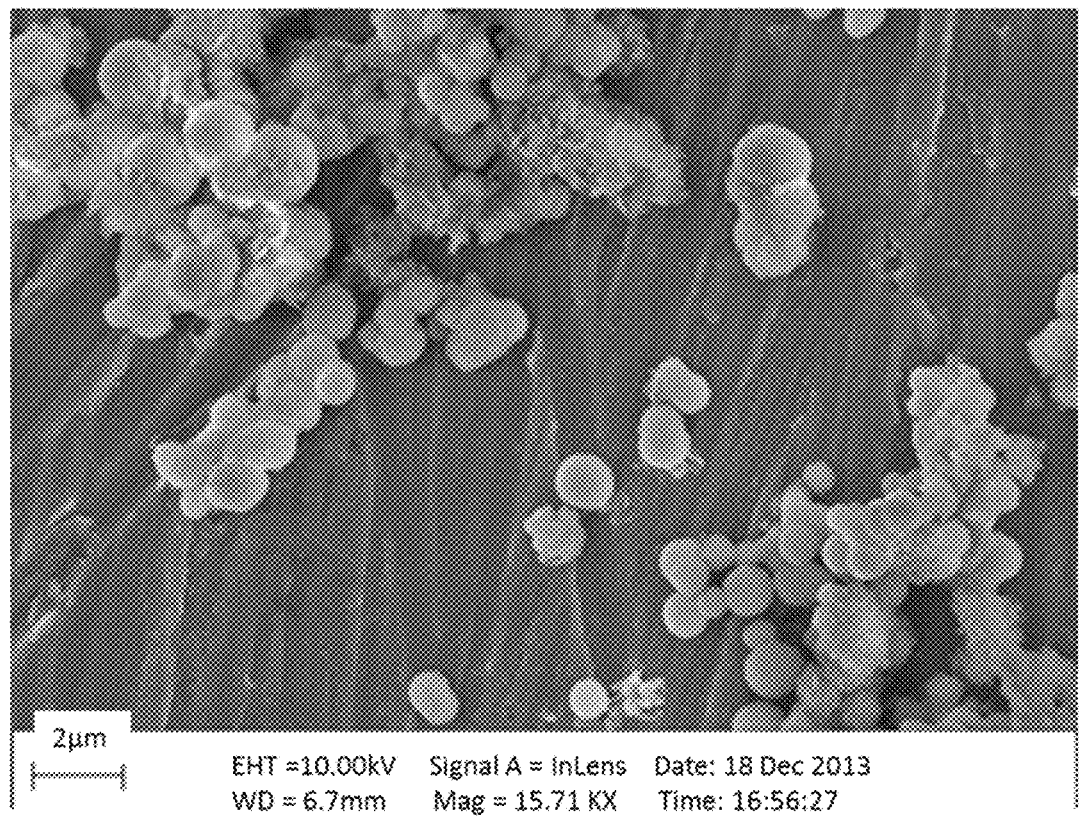
FIG. 24. SEM image of spheres after treated at 110° C. for 24 hours in Ca solution FIG. 25. XRD pattern of spheres after treated at 110° C. for 48 hours in Ca solution (*: hydroxyapatite, #: beta-TCP).
Figure 25:
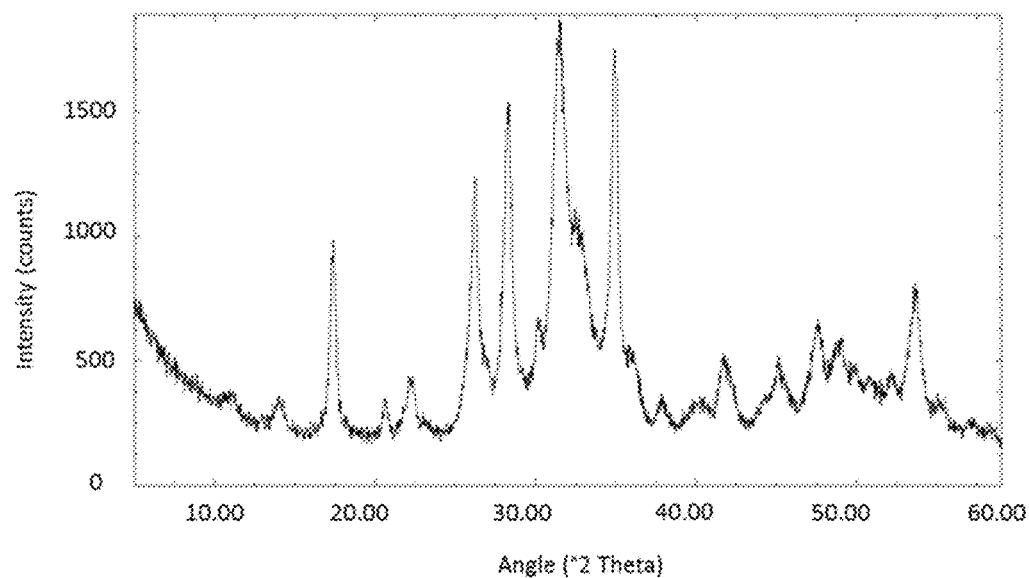

20 mg of particles obtained from Example 1 were soaked in 20 ml of calcium nitrate solution (0.5M). The mixer was then sealed in Teflon container, and stored in oven at 110° C. for 24 hours. After heat treated, the mixer was centrifuged to separate out spheres. The obtained spheres were analysed by XRD and SEM to check the crystallinity and morphology. The Rietveld refinement was used to determine phase compositions. XRD analysis shows more HA peaks appear. The refinement result shows it contains approximate 42% of HA and 58% of tri-calcium phosphate, FIG. 23. SEM image shows that the particles are still spherical, FIG. 25.

Example 13

Figure 26:
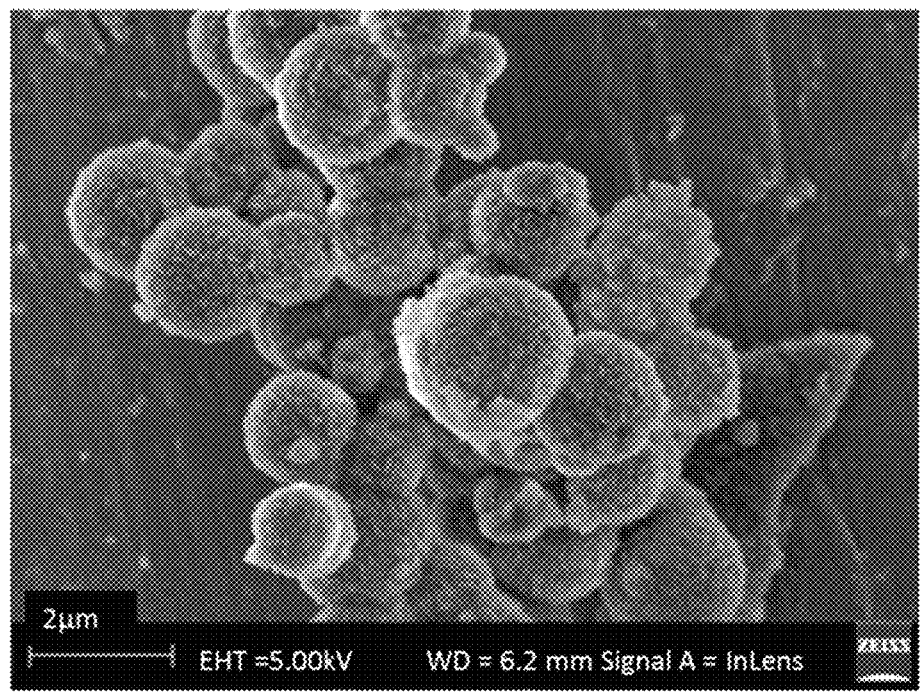
FIG. 26. SEM image of spheres after treated at 110° C. for 48 hours in Ca solution.
Figure 27:
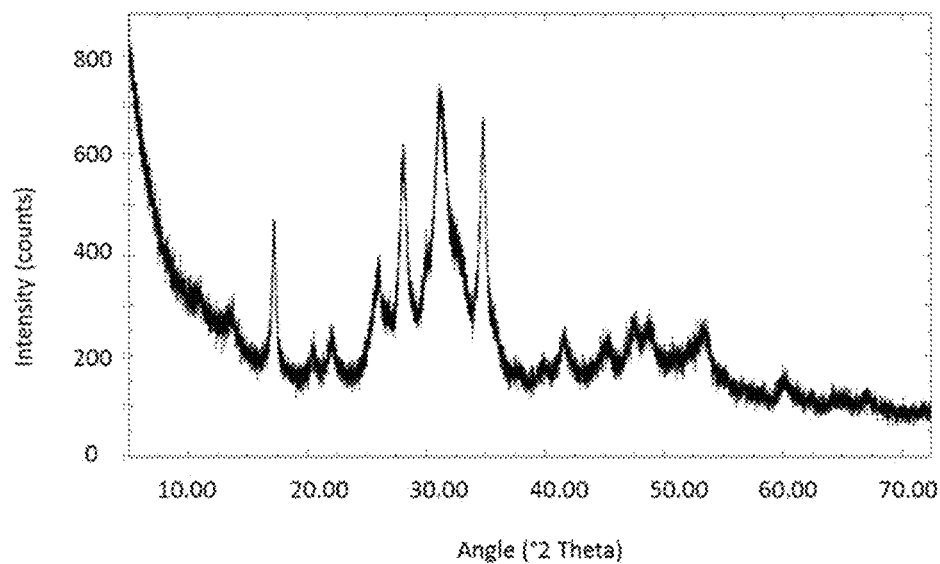
FIG. 27. XRD pattern of spheres before treatment in Ca solution.
Figure 28:
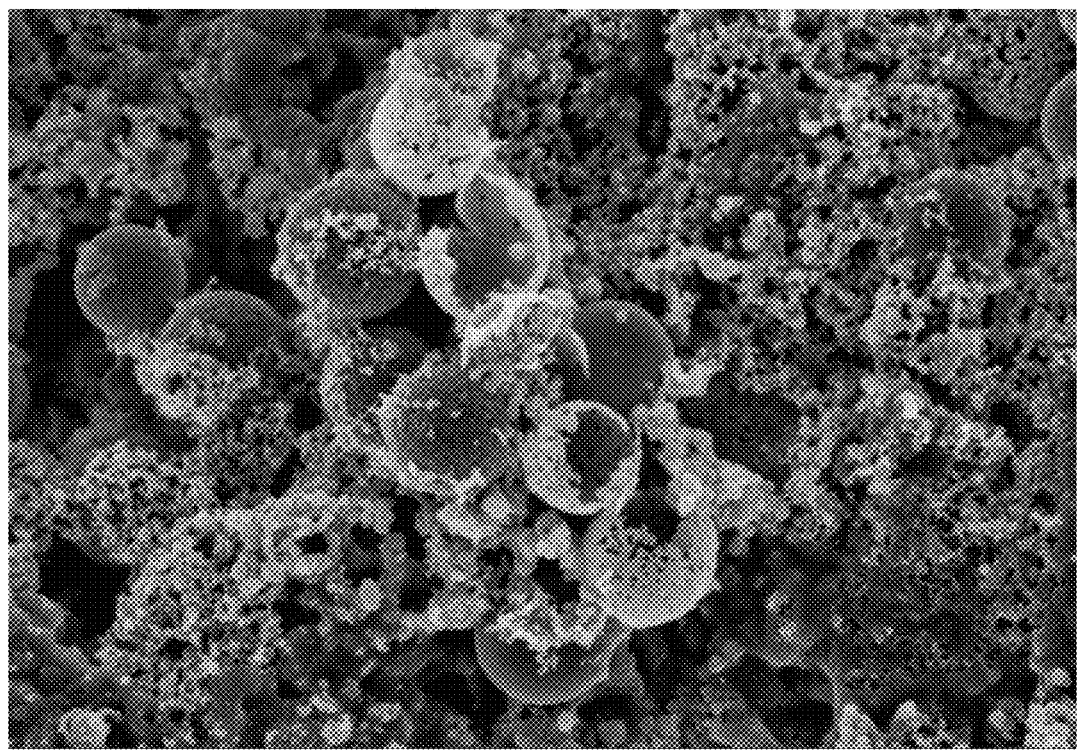
FIG. 28. Hollow particles according to the present invention.
Figure 29:
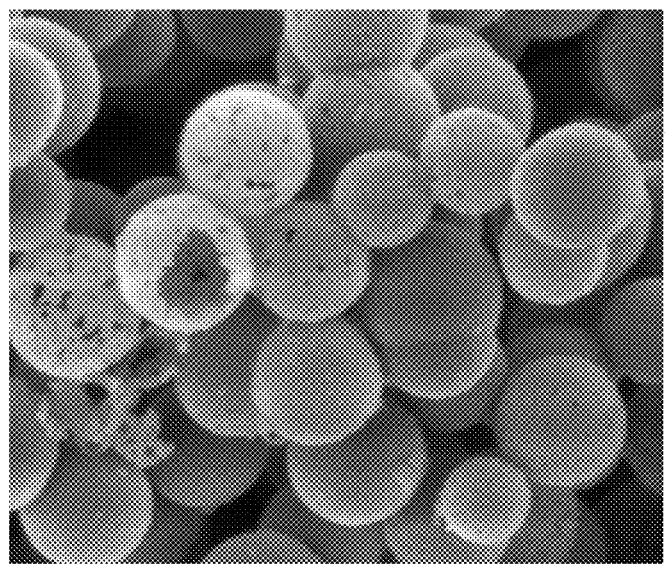
FIG. 29. Hollow particles according to the present invention.
Figure 30A:
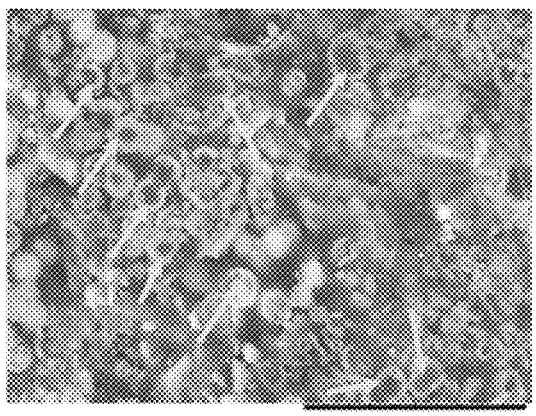
FIG. 30. A-C, hollow particles according to the present invention.
Figure 30B:
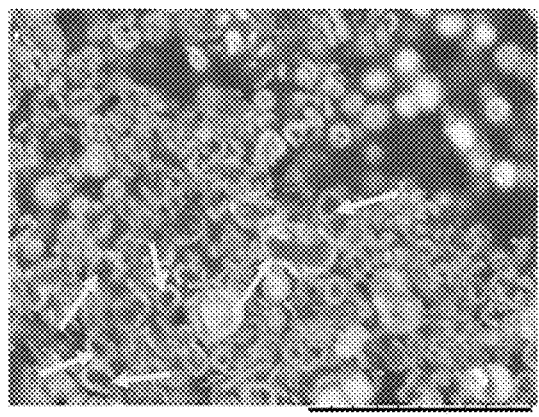
Figure 30C:
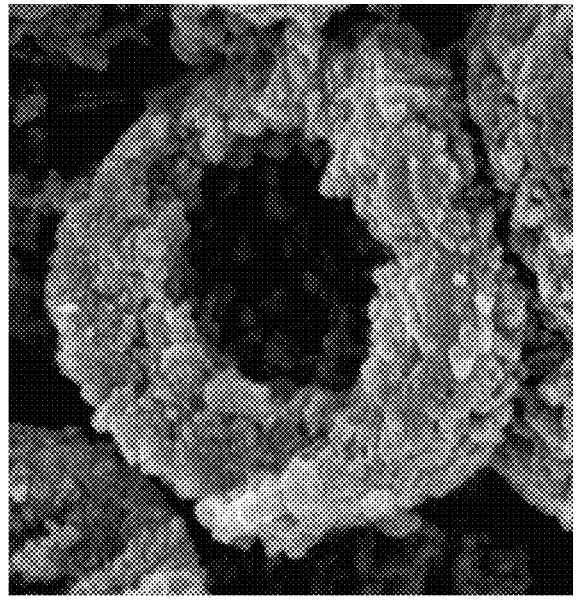
Figure 31:
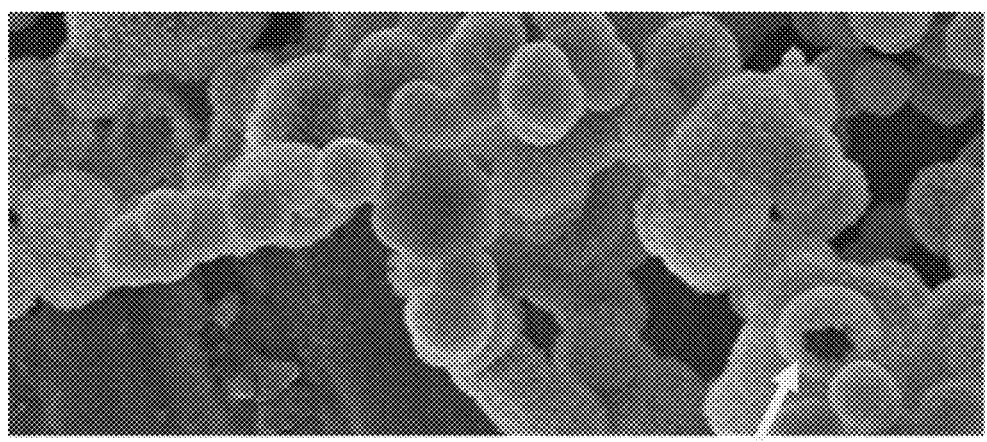
FIG. 31. Hollow particles according to the present invention.

20 mg of particles obtained from Example 1 were soaked in 20 ml of calcium nitrate solution (0.5M). The mixer was then sealed in Teflon container, and stored in oven at 110° C. for 48 hours. After heat treated, the mixer was centrifuged to separate out spheres. The obtained spheres were analysed by XRD and SEM to check the crystallinity and morphology. The Rietveld refinement was used to determine phase compositions. XRD analysis shows more HA peaks appear compared to spheres before heat treatment, and intensity of peaks is increased, FIG. 25. The refinement result shows it contains approximate 58% of HA and 42% of tri-calcium phosphate. SEM image shows that the particles are still spherical, but more flake-like crystals form on the surfaces, FIG. 26.

Example 14

An experimental set up for preparing calcium phosphate spheres by varying different parameters were performed. When varying one parameter the rest of the parameters were fixed according to the standard experimental set, pH 7.4, temperature 100° C., time 24 hours, Na:K ratio of 35:1 and a Ca: $PO_4$ ratio of 1:10.

Figure 32:
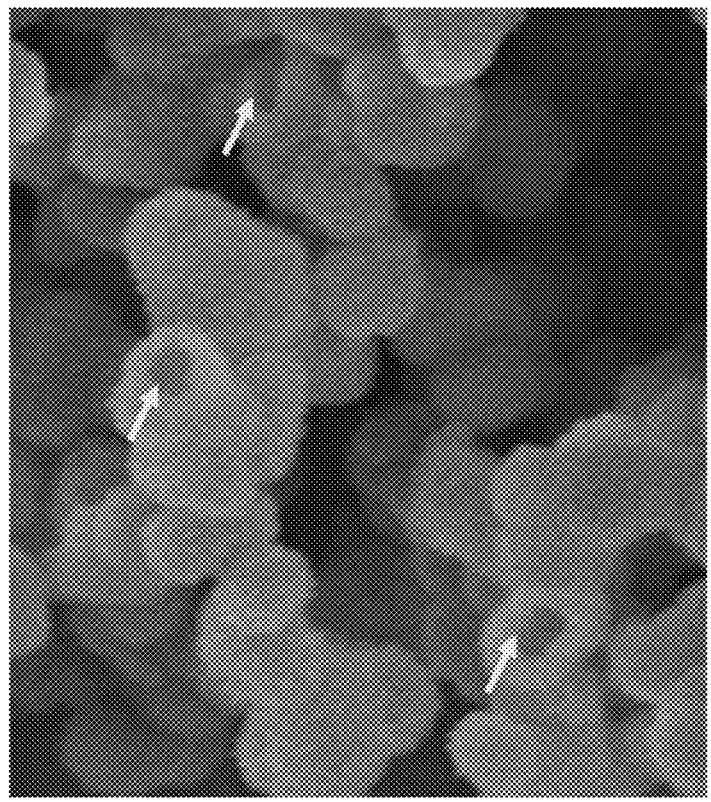
FIG. 32. Hollow particles according to the present invention.
Figure 33:
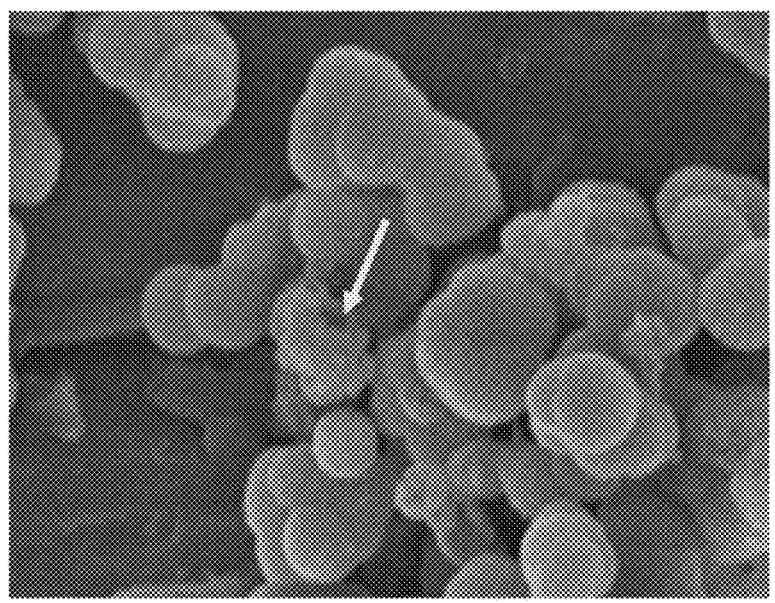
FIG. 33. Hollow particles according to the present invention.
Figure 34:
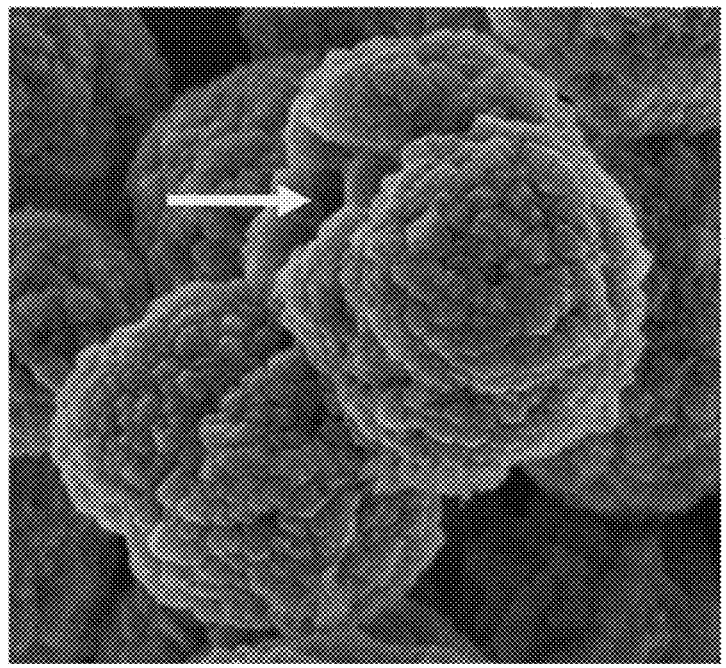
FIG. 34. Hollow particles according to the present invention.
Figure 35:
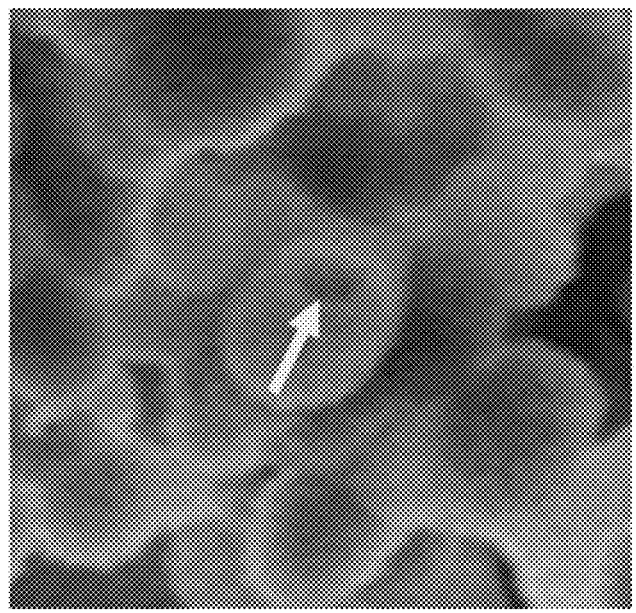
FIG. 35. Hollow particles according to the present invention.
Figure 36:
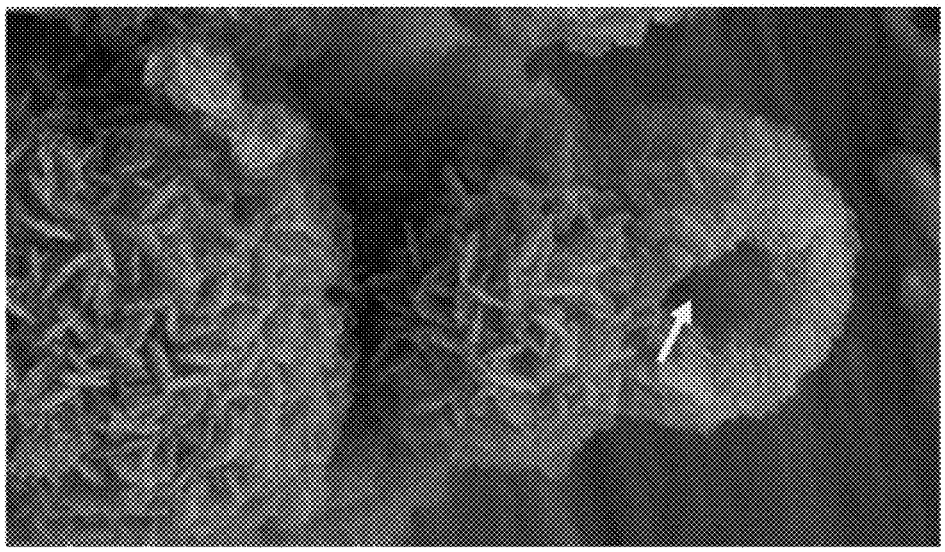
FIG. 36. Hollow particles according to the present invention.

All samples were analysed using SEM and some are disclosed in the figures. FIG. 32 shows the results from test 11, FIG. 33 shows the results from test 12, FIG. 34 from test 15, FIG. 34 from test 20, FIG. 35 from test 18 and FIG. 36 from test 19.

| Test | pH | Temp. (° C.) | Time (h) | [Na]* | [K]** | [PO₄]$^a$ | [Ca]$^b$ | Comment |
|---|---|---|---|---|---|---|---|---|
| 1 | 5.0 | | | | | | | No spheres$^c$ |
| 2 | 8.0 | | | | | | | Hollow spheres |
| 3 | | 60 | | | | | | Spheres, some hollow |
| 4 | | 150 | | | | | | Hollow spheres |
| 5 | | | 0.03 | | | | | Spheres |
| 6 | | | 0.17 | | | | | Spheres, some hollow |
| 7 | | | 1 | | | | | Hollow spheres |
| 8 | | | | 20 | | | | No spheres |
| 9 | | | | 60 | | | | No spheres |
| 10 | | | | 100 | | | | Hollow spheres |
| 11 | | | | 200 | | | | Hollow spheres |
| 12 | | | | | 0.1 | | | Hollow spheres |
| 13 | | | | | 1 | | | Hollow spheres |
| 14 | | | | | 2 | | | Hollow spheres |
| 15 | | | | | 5 | | | Hollow spheres |
| 16 | | | | | 10 | | | Hollow spheres |
| 17 | | | | | | 4.78 | | Hollow spheres |
| 18 | | | | | | 2.38 | | Hollow spheres |
| 20 | | | | | | 0.95 | | Hollow spheres |
| 21 | | | | | | | 0.1 | Hollow spheres |
| 22 | | | | | | | 2 | No spheres |

*concentration in mM and a [K] of 2.68 mM
**concentration in mM and a [Na] of 136.9 mM
$^a$concentration in mM and [Ca] is 1 mM
$^b$concentration in mM and [PO₄] is 10 mM
$^c$No precipitation was formed

The invention claimed is:

1. Spherical particles having a hollow core and a shell wherein the particle comprises 40-70 weight % of calcium, 20-40 weight % of phosphate and 3-15 weight % magnesium, and wherein the Ca/P weight ratio is in the range of 1.10 to 1.90, and wherein more than 80% of the particles have a mean particle size between 200 to 600 nm, and wherein the particles are free from strontium.

2. A composition comprising spherical particles according to claim 1, and a paste forming compound.

3. The composition of claim 2, wherein the crystallinity of the particle is at least 10%.

4. The composition according to claim 2, wherein the mean particle size is 550-600 nm.

5. The composition according to claim 2, wherein the shell of the particle is porous.

6. The composition according to claim 2, wherein the particle comprises 55-65 weight % of calcium, 25-35 weight % of phosphate and 4-8 weight % magnesium and wherein the Ca/P ratio is in the range of 1.40-1.50.

7. The composition according to claim 2, wherein the particle further comprises at least one of ions selected from silicon, zinc, and fluoride.

8. The composition according to claim 2, wherein the content of particles is at least 0.5 weight %.

9. A bleaching paste comprising the composition according to claim 2, wherein the particles further comprises a peroxide.

10. A toothpaste comprising the composition according to claim 2.

11. An implant comprising particles according to claim 1.

12. A bone void filling material comprising particles according to claim 1.

13. A dental filling material comprising the particles according to claim 1.

14. A method of treating exposed dental tubuli and/or for remineralization of teeth comprising applying the composition of claim 1 to teeth.

15. The composition of claim 2, wherein the crystallinity of the particle is at least 50%.

16. The composition of claim 2, wherein the crystallinity of the particle is at least 75%.

* * * * *